United States Patent
Tuli

(10) Patent No.: US 12,279,935 B2
(45) Date of Patent: Apr. 22, 2025

(54) METHOD OF MANUFACTURING A DIAPER WITH MOISTURE SENSORS

(71) Applicant: Raja Singh Tuli, QC (CA)

(72) Inventor: Raja Singh Tuli, QC (CA)

(*) Notice: Subject to any disclaimer, the term of this patent is extended or adjusted under 35 U.S.C. 154(b) by 611 days.

(21) Appl. No.: 16/033,200

(22) Filed: Jul. 12, 2018

(65) Prior Publication Data

US 2019/0240080 A1    Aug. 8, 2019

Related U.S. Application Data

(63) Continuation-in-part of application No. 15/890,901, filed on Feb. 7, 2018, now Pat. No. 11,191,678.

(51) Int. Cl.
*A61F 13/42*    (2006.01)
*A61F 13/15*    (2006.01)
(Continued)

(52) U.S. Cl.
CPC ........ *A61F 13/42* (2013.01); *A61F 13/15699* (2013.01); *A61F 13/15723* (2013.01);
(Continued)

(58) Field of Classification Search
CPC .......... A61F 13/15723; A61F 13/15764; A61F 13/42; A61F 13/49; A61F 2013/15829; A61F 2013/424; A61F 2013/429
See application file for complete search history.

(56) References Cited

U.S. PATENT DOCUMENTS

| 4,106,001 A | 8/1978 | Mahoney |
| 5,790,036 A * | 8/1998 | Fisher ............... A61F 13/42 |
| | | 128/886 |

(Continued)

*Primary Examiner* — Catharine L Anderson
*Assistant Examiner* — Lynne Anderson

(57) ABSTRACT

The present invention discloses a method of manufacturing a diaper that has multiple moisture sensing elements on interior side of its bottom impermeable layer or on any surface of the top permeable layer. The moisture sending elements are made by spraying conductive ink on a moving sheet of either the bottom impermeable layer or the top permeable layer, before other layers of the diaper are attached. Spraying of conductive ink on the moving sheet causes parallel lines of conductive inks to be formed on the layer. The parallel lines of conductive ink run through the entire length of either of the layers and are designed to get connected with a detecting device. When a user urinates inside the diaper, the moisture causes a closed circuit between at least two of the parallel lines of conductive inks. These formations of closed circuits, between parallel lines of conductive inks, are detected by the detecting device. Also, with increasing volume of moisture, the resistance of the closed circuits also tends to decrease. This rate of decrease of resistance is also detected by the detecting device and is used to calculate a volume of moisture present in the diaper. The detecting device then generates a suitable alarm to give an idea about the saturation level of the diaper. The process of manufacturing sensing elements by spraying conductive inks on moving sheet of layer reduces the processing and modification overhead of specially designed conductive ink printers and also does not impact the manufacturing time of a diaper manufacturing assembly line.

7 Claims, 23 Drawing Sheets

(51) Int. Cl.
*A61F 13/49* (2006.01)
*G01N 27/12* (2006.01)

(52) U.S. Cl.
CPC .. *A61F 13/15764* (2013.01); *A61F 13/15804* (2013.01); *A61F 13/49* (2013.01); *G01N 27/12* (2013.01); *A61F 2013/15829* (2013.01); *A61F 2013/424* (2013.01); *A61F 2013/429* (2013.01)

(56) References Cited

U.S. PATENT DOCUMENTS

| | | | |
|---|---|---|---|
| 5,808,554 A | | 9/1998 | Shuminov |
| 5,838,240 A | | 11/1998 | Johnson |
| 6,175,310 B1 | * | 1/2001 | Gott .................... G01M 3/165 |
| | | | 340/604 |
| 6,200,250 B1 | | 3/2001 | Janszen |
| 6,559,772 B2 | | 5/2003 | Zand et al. |
| 7,956,754 B2 | | 6/2011 | Long |
| 7,977,529 B2 | | 7/2011 | Bergman et al. |
| 8,884,769 B2 | | 11/2014 | Novak |
| 9,291,589 B2 | | 3/2016 | Wong et al. |
| 9,498,394 B2 | * | 11/2016 | Hu .................... A61F 13/49058 |
| 2007/0156106 A1 | | 7/2007 | Klofta et al. |
| 2011/0319845 A1 | | 12/2011 | Kuo et al. |
| 2020/0046573 A1 | * | 2/2020 | Douseki ................ A61F 13/42 |
| 2020/0163805 A1 | * | 5/2020 | Lee ........................ B29B 13/08 |

* cited by examiner

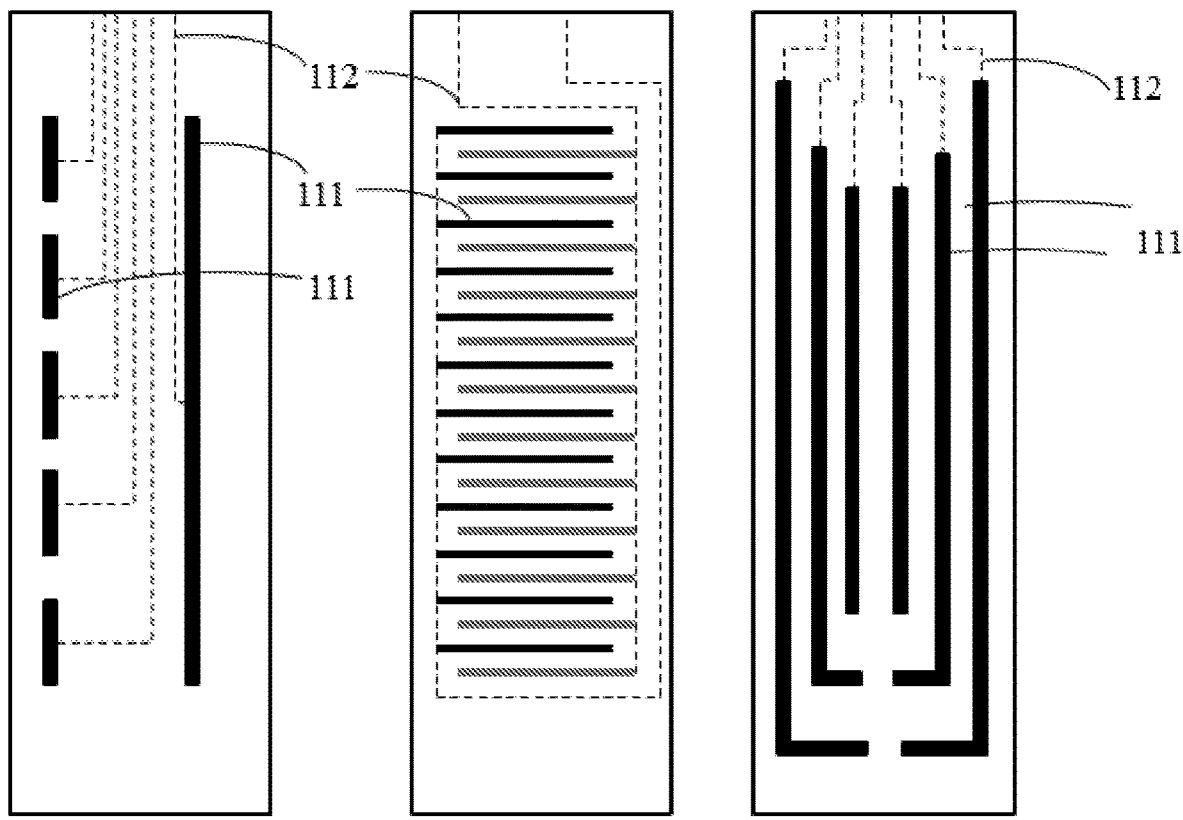
FIG. 1B
(Prior Art)
FIG. 1C
(Prior Art)
FIG. 1D
(Prior Art)
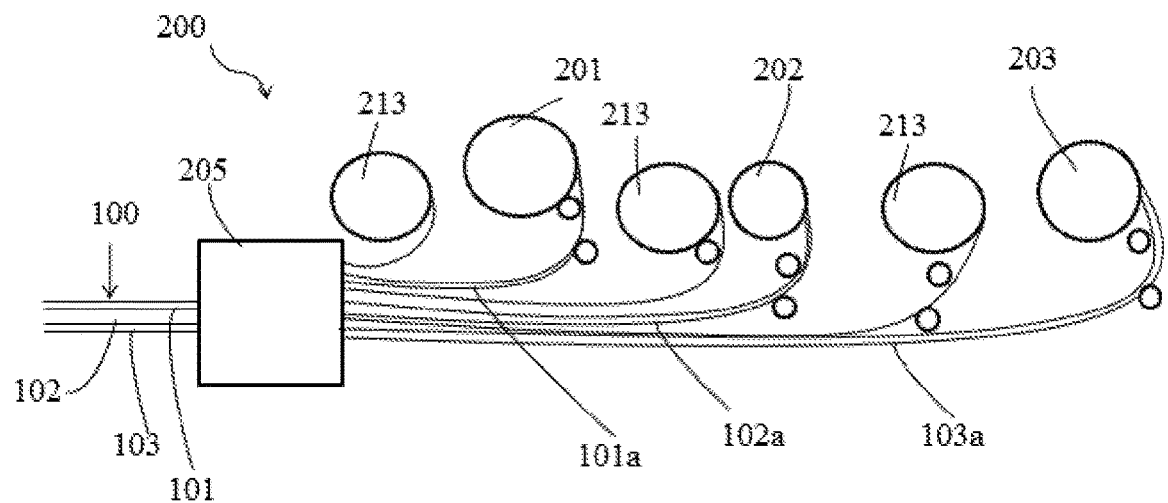
FIG. 2
(Prior Art)

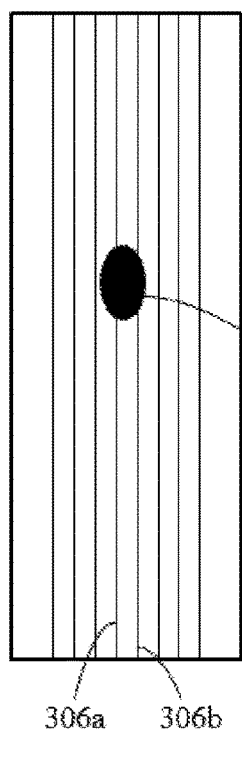 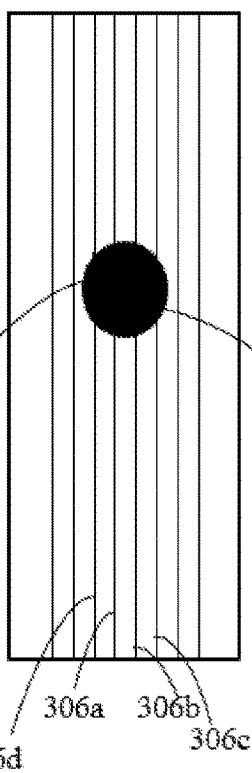 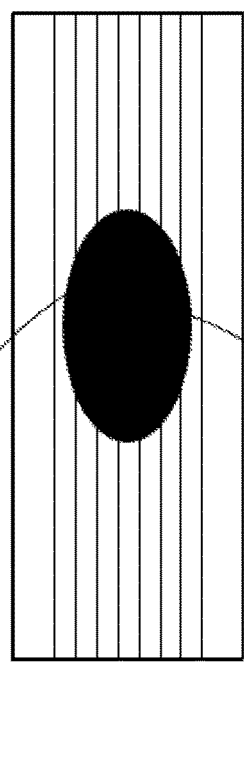 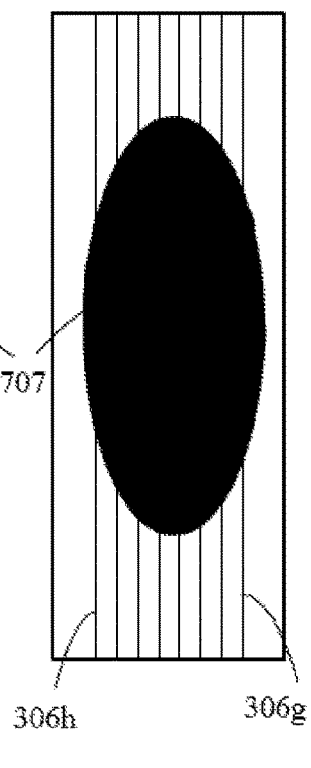
FIG. 7A　　FIG. 7B　　FIG. 7C　　FIG. 7D
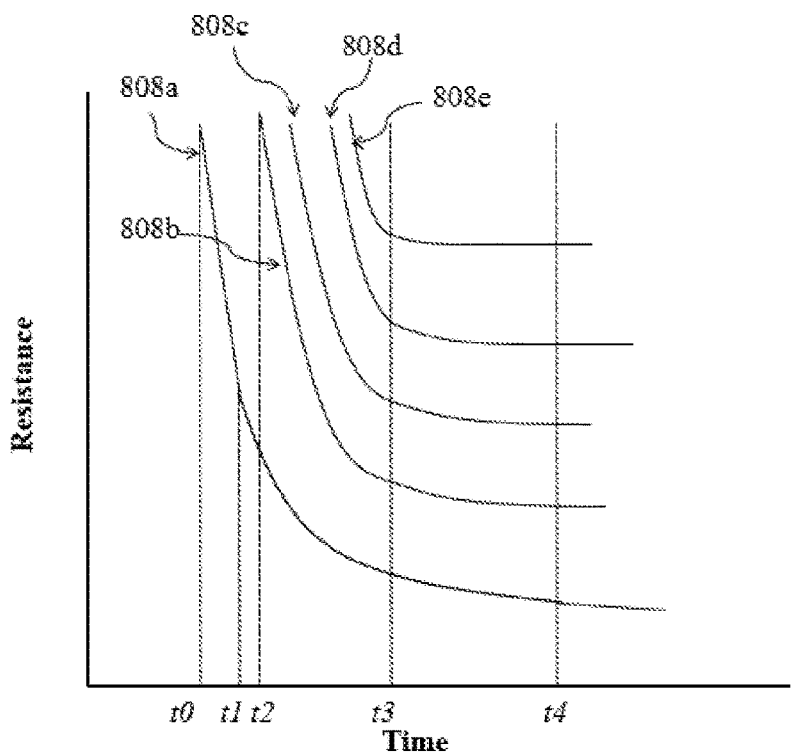
FIG. 8A

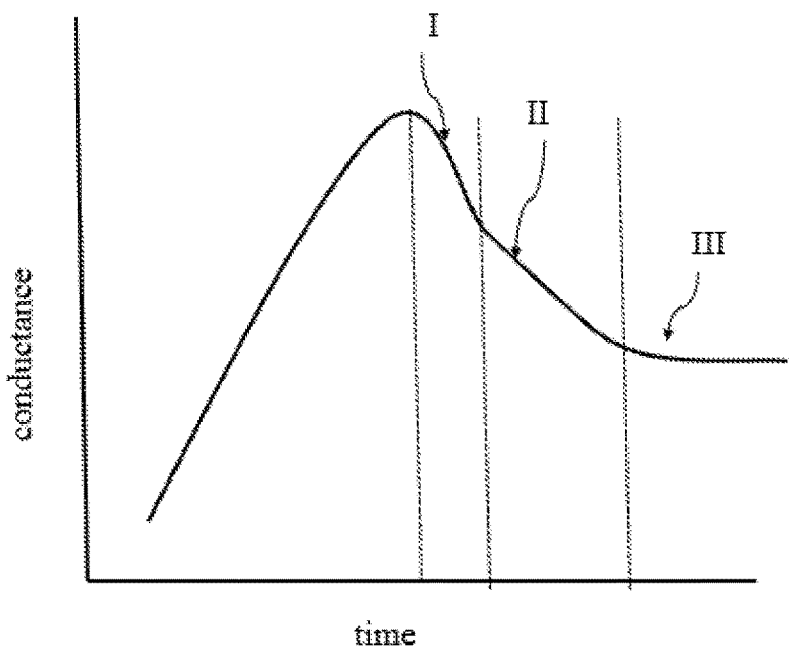
FIG. 22C
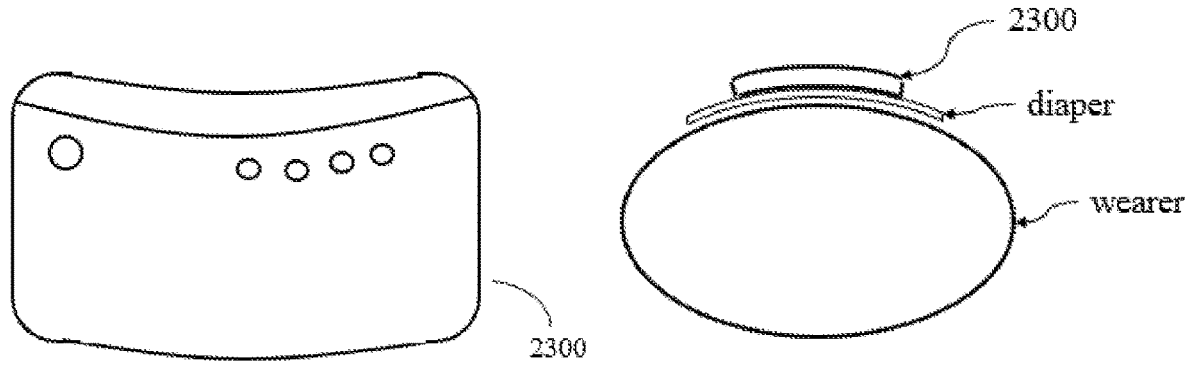
FIG. 23A
FIG. 23B

METHOD OF MANUFACTURING A DIAPER WITH MOISTURE SENSORS

CROSS-REFERENCE TO RELATED APPLICATIONS

This application is a continuation-in-part of U.S. patent application Ser. No. 15/890,901 filed Feb. 7, 2018

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not Applicable

STATEMENT REGARDING PRIOR DISCLOSURES BY THE INVENTOR OR A JOINT INVENTOR

Not Applicable

BACKGROUND

Field of the Invention

This invention relates to devices for manufacturing absorbent materials, such as diapers, wherein moisture detecting elements are present on an inner layer of the diaper.

Description of Related Art

For many years, a variety of designs have been developed for detecting and signalling the presence of urine in a diaper. However, most of these designs require manufacturing modifications to ordinary diapers in order to be implemented. With manufacturing modifications, lot of changes and additional machineries are required to be implemented in the manufacturing process of the diaper. Other designs use conductive leads as sensors to detect changes in electrical property of a diaper due to urination. Such sensors can also be placed over an inner layer of a diaper such that the sensors face user of the diaper. Even though lot of care is taken to make such sensors from materials that do not cause irritation to the user, the satisfaction of the user remains doubtful. Another way of detecting moisture inside a diaper is to use temperature sensors. In U.S. application Ser. No. 11/589,414, a temperature sensor is fastened to an interior surface of a diaper. A window or a cut out or a pocket on the diaper is present to make the temperature sensor visible from outside. However, the window is provided with a thermal insulating feature to avoid ambient temperature to affect the temperature sensor. However, such kind method to detect presence of moisture in a diaper using temperature sensor would require modifications in manufacturing process of an ordinary diaper.

In U.S. Pat. No. 6,559,772, moisture in a diaper is sensed using a wick strip made up of conductive inks that is inserted inside an ordinary diaper. This wick strip is connected to an alarm unit, where the presence of moisture is being detected using the conductive ink strips. However, this kind of diapers with temperature sensors would also require manufacturing e 2 modifications in ordinary diaper and also will require specialized printers to make the conductive ink based wick.

U.S. Pat. No. 6,200,250 discloses a method of manufacturing a diaper having moisture sensing elements. Those elements can be of many types including filaments, wires, yarn, ribbon, foil, fabric or film made from conductive material such as conductive inks. However, this kind of manufacturing requires the conductive ink to be printed or rolled. Thus, the overall manufacturing process of the diaper needs to be added with specialized printers or other machinery to print the conductive ink based elements inside the diaper.

U.S. Pat. No. 5,808,554 discloses a moisture detecting liner for a diaper and a process of manufacturing the same. The moisture detecting liner is made up of several electrically conductive tracks that are made up of conductive inks. The tracks are designed so as to cover maximum space within the diaper. These tracks need to be printed using specialized printers which add additional machinery and complications to the method of manufacturing an ordinary diaper.

U.S. Pat. No. 7,956,754 discloses a diaper having wetness sensors to detected presence of moisture inside the diaper. The wetness sensor is constructed from conductive inks that are printed on a chassis or one of the layers of the diaper. To make the wetness sensors cover a maximum area within the diaper, the wetness sensors are designed in a serpentine way and hence, needs specialized printers to print the wetness sensors on any one the layers. Such a type of sensors, even though can detect presence of moisture and location of moisture in a diaper, impacts the manufacturing process of the diaper as it requires additional printers to be introduced in the manufacturing process and hence, are unfeasible to be implemented in a assembly line of manufacturing diapers.

Also, all existing conductive ink based moisture sensors are designed in such a way that they require specialized printers to print those sensors inside a layer of ordinary diapers. Introduction of a printer not only increases the operational complexity of manufacturing a diaper, but also increases the time of manufacturing a diaper. Hence, there is a need for a moisture sensor based diaper that can be manufactured easily without impacting the process flow of manufacturing an ordinary diaper, and without increasing costs associated with introducing specialized printers for printing the moisture.

BRIEF SUMMARY OF THE INVENTION

The invention described herein depicts a moisture sensing and alerting system comprising a detecting device and a diaper with sensor elements. It is intended that the sensor elements as per one of the embodiment of the present invention is placed on an internal side of a bottom impermeable layer of an ordinary diaper. One objective of the present invention is to provide multiple sensor elements that are drawn on an interior side of the bottom impermeable layer of an ordinary diaper, wherein the sensor elements are drawn on the bottom impermeable layer during manufacturing process of the ordinary diaper. The sensor elements are drawn on the bottom permeable layer by spraying conductive carbon ink or similar types of conducting inks. The sensor elements are connected to a detecting device, such that moisture present on the ordinary diaper can be sensed and a suitable alert can be generated.

According to an aspect of the present invention, the sensor elements are drawn on the internal side of a bottom permeable layer of a diaper during the manufacturing process using an ink sprayer. Diapers are made using assembly lines where multiple layers of diapers are combined together and cut to form a diaper core. Attachment strips like Velcro™ and/or elastic tapes are added to the diaper core and a final ordinary diaper is made. Within one of the roller equipment of the assembly line delivering a bottom impermeable layer of diaper, an ink sprayer is attached right before the other layers are being placed on it. The ink sprayer provides conductive ink lines on the interior portion of the impermeable layer. The sprayer can be one single ink sprayer having multiple nozzles to create multiple ink lines that act as sensor elements. Also, multiple ink prayers can be used to create separate sensor elements.

In yet another aspect of the present invention, a pen/pencil like apparatus is used to draw conductive ink lines on the inner surface of the bottom plastic layer before other diaper layers are applied on top of the bottom plastic layer. The pen/pencil like apparatus can also be a single apparatus having multiple nibs separated from each other to create multiple conductive ink lines or multiple pens/pencils drawing separate conductive ink lines on the bottom plastic layer. The number of sprayers/pens/pencils or number of nozzles of the sprayer/nibs of pen/nibs of pencils is same as the number of sensor elements that are to be present inside the bottom plastic layer.

In yet another embodiment of the present invention, the volume of the moisture present inside a diaper can be detected using the sensor elements. The sensor elements are drawn as parallel lines of conductive inks running throughout the length of the bottom impermeable layer of the diaper, such that the sensor elements cover area from front to back of a user wearing the diaper. When moisture gets settled inside the diaper, the moisture forms a closed connection between two adjacent sensor elements and with increasing volume of moisture, the resistance between the adjacent sensor elements continues to decrease. At the same time, more adjacent sensors start to form closed connections as the moisture continues to increase. Hence, with increase in volume of moisture, more closed connections are formed and slowly resistance between each of the sensor elements starts to decrease. Rate of decrease of resistance is directly related to the volume of the moisture and this provides an indication of the amount of moisture that is present in the diaper. The more the moisture, faster the resistance will drop.

A detecting device is attached to the diaper from outside and it can be removably coupled to an extended portion of the bottom permeable layer such that it forms a resilient connection with the sensor elements. The detecting device comprises of processors and other electronic circuits that detects change in resistance and formation of closed circuits due to the moisture, and generates a suitable alert. The detecting device can provide an alert signal or the like by wireless means or wired means. The detecting device can be attached to the diaper using any known-in-the-art mechanisms such that the detecting device gets electrically coupled with the sensor elements.

In another embodiment, the sensor elements can be used to detect various levels of moisture present inside a diaper. Since, the sensor elements run length wise throughout the internal surface of the bottom impermeable layer of a diaper, the moisture inside touches various different sensor elements at different times based on the volume of moisture. Moisture excreted by a user will first be in touch with the sensor elements that are present on a central portion of the exterior layer. With increasing volume of moisture, sensor elements that are present on edge portions will also be in contact with the moisture. Hence, the detecting device can sense when the moisture has reached the sensor elements present on the edge portion and thus generate an alert about saturation level of the diaper.

In another embodiment of the invention, the sensor elements are sprayed on a top of permeable layer of an ordinary diaper using a sprayer close to a roller equipment supplying sheet of top permeable layer to a diaper manufacturing assembly line. When a user urinates inside the diaper, at first, the urine forms a closed circuit between at least two of the adjacent sensor elements on the top permeable layer. With time, the urine gets soaked inside the diaper and then the closed circuit breaks. When a closed circuit is formed, the resistance between the two sensor elements starts to decrease and when the urine gets soaked inside, the resistance starts to rise till the time the closed circuit breaks. Again, when a user urinates, a closed circuit is formed which gets broken when the urines is absorbed inside the diaper. With increasing volume of urine soaked inside the diaper, the time for absorption will increase. Thus a closed circuit will remain closed for a longer duration of time. Eventually, a time will come, when the diaper gets saturated and the urine will get soaked inside very slowly. That will cause a closed circuit and fall in resistance for a very long period f time. This formation, duration and resistance of closed circuits can be processed by the detecting device to estimate various level of saturation of the diaper. The detecting device can then generate various alerts to indicate the saturation levels and also volume of urine inside the diaper.

As per yet another embodiment of the present invention, the sensing electrodes are pre-printed on a roll of diaper layer using any of the method known in the art. However, the design of the sensing electrode is such chosen that the machine does not have to register the design and can cut pieces of diaper at any location. The design is such chosen that a detecting device can connect to all the sensing electrode of the diaper, irrespective of the location at which the diaper is cut from a diaper roll. As per the sensing electrode design present in the previous embodiments, the diaper manufacturing machine have to know the precise location within which rolling sheet of diaper needs to be cut. As per this embodiment of the present invention, the diaper manufacturing machine can cut through a sheet of diaper at any location and yet, the moisture sensing capability of the diaper remains intact.

BRIEF DESCRIPTION OF THE DRAWINGS

The various preferred embodiments of the present invention described herein can be better understood by those skilled in the art when the following detailed description is read with reference to the accompanying drawings. The components in the figures are not necessarily drawn to scale and any reference numeral identifying an element in one drawing will represent the same element throughout the drawings.

The figures of the drawing are briefly described as follows:

FIG. 1B-1D is a top view of moisture sensors known in the art.

FIG. 2 is a plan view of an assembly line used for manufacturing an ordinary diaper.

FIGS. 7A-7D is a top view of an interior side of a bottom impermeable sheet of a diaper with increasing volume of moisture as per one of the embodiment of the present invention.

FIG. 8A is a graph depicting formation of closed circuits and their resistance with respect to time.

FIGS. 22A-22C describe detection of moisture inside the bottom layer of the diaper as per another embodiment of the present invention.

FIGS. 23A-23B illustrate a detecting device to be used with the diaper as per the another embodiment of the present invention.

DETAILED DESCRIPTION OF THE INVENTION

The present invention discloses a moisture detecting and alerting system comprising a diaper having multiple sensor elements and a portable detecting device, preferably of non-disposable type, electrically coupled to the sensor elements. The purpose of the present invention is to provide a method to provide the sensor elements on any layer of any ordinary diaper without requiring any specialized conductive ink printers. The sensor elements, as per the present invention, are straight lines of conductive inks that are provided on any layer/s of the multiple layers of an ordinary diaper using sprayers or pens or sketch-pens, before all the layers are combined to form a final diaper on a moving assembly line. When a user urinates inside the diaper, urine traverses through a top permeable layer and gets soaked inside an absorbent layer of the diaper, where it is kept in place by the bottom impermeable layer. Thus, the urine comes in contact with the sensor elements present either on the bottom impermeable layer or on the top permeable layer, and causes a closed circuit between at least two of the sensor elements. This closed circuit is sensed by the portable detecting device and a suitable alarm is generated to indicate presence of urine inside the diaper. When the sensor elements are placed on a bottom impermeable layer, with increasing volume of body fluid, more closed circuits are formed and resistance of the already existing closed circuits starts to decrease. The rate of decrease of the resistance and increasing number of closed circuits, are detected by the portable detecting device. The portable detecting device then can generate an alarm indicating volume of moisture inside the diaper based on the rate of decrease in the resistance. When the sensor elements are present on a top permeable layer, the urine will form a closed circuit between at least two adjacent sensor elements for duration of time before the urine gets soaked inside the absorbent layer. With increasing volume of urine, the closed circuit will remain for a longer duration of time as the diaper starts to get saturated. The portable detecting device can track the formation of closed circuits, resistances and durations of the closed circuits to identify saturation level of the diaper. A suitable alarm is generated based on the saturation level of the diaper.

Figure 1A:
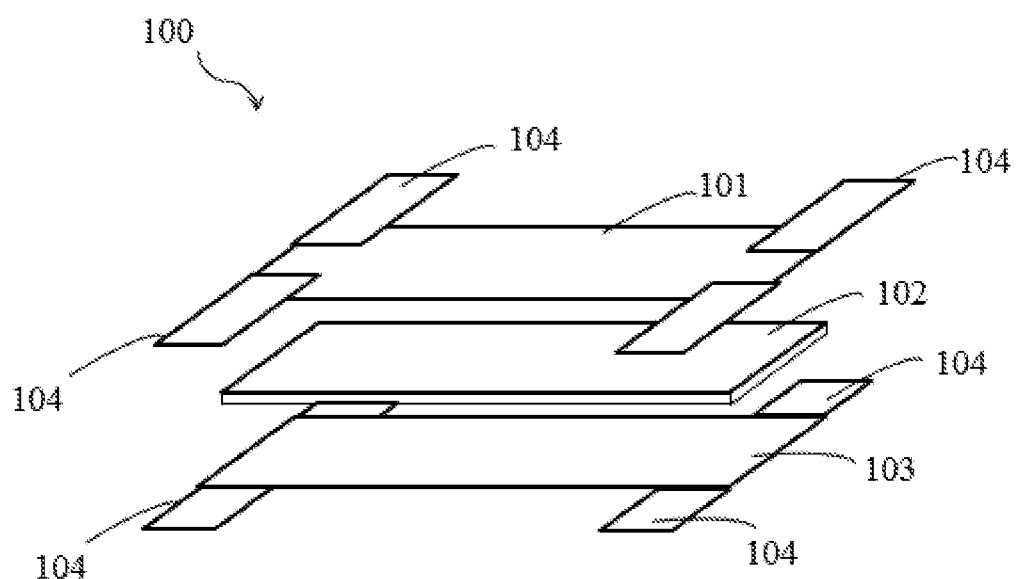
FIG. 1A is a perspective view of different layers in an ordinary diaper.

FIG. 1 illustrates a perspective view of an ordinary disposable diaper 100. The disposable diaper 100 primarily consists of an absorbent pad 102 sandwiched between two sheets of nonwoven fabric. The absorbent pad 102 is specially designed to absorb and retain body fluids, and the nonwoven fabric gives the diaper a comfortable shape and helps prevent leakage. These diapers are made by a multi-step process in which the absorbent pad 102 is first vacuum-formed, then attached to a permeable top sheet 101 and an impermeable bottom sheet 103. Other layers of cloth and plastic type material are also added in-between the absorbent pad and the two sheets of non-woven fabric as intermediate layers (not shown). The intermediate layers can contain various types of sensors like moisture sensors, temperature sensors or other type of sensors. All of these components are sealed together by application of heat or ultrasonic vibrations. Elastic fibers or tapes or similar attaching means 104 like Velcro, are attached to the sheets to gather the edges of the diaper 100 into the proper shape so it fits snugly around a user's legs and crotch. When properly fitted, the diaper 100 will retain body fluids which pass through the permeable top sheet 101, are absorbed into the absorbent pad 102 and kept inside by the impermeable bottom sheet 103.

FIG. 1B-1D illustrates various types of moistures sensors that are used in ordinary diapers 100 that are known in the art. These moisture sensors have sensing elements 111 and conductors 112 that connect the sensing elements 111 to a detecting device. The moisture sensors are generally printed with inkjet printers or other specialized printers on any layer of an ordinary diaper. In known in the art technologies, such sensors are also printed either on the top permeable sheet 101 or the bottom impermeable sheet 103 of the ordinary diaper 100. In some existing technologies, the moisture sensors are also printed on any one of the sides of the absorbent pad 102. The sensing elements 111 are designed in such a way that they do not touch each other when the ordinary diaper 100 is dry. When a user urinates inside the ordinary diaper 100, urine forms an electrical closed connection between any two of the sensing elements 111 and that is detected by a detecting device. The sensing elements 111 are designed to spread across various locations along the length of the ordinary diaper 100 so as to know the location of urine. An insulating layer is provided on top of the moisture sensors, such that the insulating layer overlaps the conductors 112 and exposes 111 to moisture, so as to identify locations of moisture accurately. The insulating layer acts as an open circuit insulation between any two sensing elements 112 that gets closed only when moisture is present. The sensing elements 111 and conductors 112 are both made from conductive inks and hence special ink-jet based printers are required to have distinctive designs of the sensing elements 111 and conductors 112. Also, addition of an insulating material also changes the manufacturing process required to make an ordinary diaper.

FIG. 2 illustrates an assembly line 200 used for manufacturing the ordinary diaper 100 as known in the prior art. Generally such processes are known as roll-to roll process as multiple rolls of materials are combined one on top of other and combined to form a final diaper. The absorbent pad 102 is composed of two essential elements, a hydrophilic, or water-loving, polymer and a fibrous material such as wood pulp. The polymer is made of fine particles of an acrylic acid derivative, such as sodium acrylate, potassium acrylate, or an alkyl acrylate. These polymeric particles act as tiny sponges that retain many times their weight in moisture. The absorbent pad 102 is formed on a movable conveyer belt (not shown) that passes through a long forming chamber where polymers and fibers are mixed to form a sheet of absorbent pad 102a, which then proceeds down a conveyor path to a levelling roller near the outlet of the forming chamber. This roller removes a portion of the fibers at the top of the pad to make it a uniform thickness. The sheet of absorbent pad 102a then moves by the conveyor through the outlet for subsequent operations to form the completed diaper 100 in the assembly line 200 through roller equipment 202. The absorbent pad 102 is held in place by nonwoven fabric sheets that form the body of the diaper 100. Nonwoven sheets are typically made from plastic resins, such as nylon, polyester, polyethylene, or polypropylene, and are assembled by mechanically, chemically, or thermally interlocking the plastic fibers. Polypropylene is typically the material used for the permeable top sheet 101, while polyethylene is the resin of choice for the impermeable back sheet 103. These sheets are produced as a wide roll known as a web, which is then cut to the appropriate width for use in diapers. There are two separate webs of long rolls of sheets for the permeable top sheet 101a and another for the impermeable bottom sheet 103a. Both of these sheets are supplied to the assembly line 200 using two separate roller equipments—201 and 203. In between these three primary sheets, other intermediate layers 113, some of which are plain cloth based layers and some are plastic based layers, are also added based on the type of the ordinary diaper 100 that is intended to be manufactured using the assembly line 200. These intermediate layers are supplied through multiple roller equipments 213. The roller equipments 213 can be placed on any order in the assembly line based on in-between which layers these intermediate layers needs to be added. The other intermediate layers 113 can also be added to obtain various other features. Some of the other layer 113 may also contain different types of sensors imprinted on them. All these layers of sheet materials then pass through a pressure chamber 205 where all these three sheets are joined by gluing, heating, or ultrasonic welding to generate a long sheet of diaper 100. Then the long sheet of diaper is cut into appropriate diaper sizes and attachment mechanisms such as strips of tape or Velcro™ are attached that act as closures of the final disposable diaper 100.

Figure 3A:
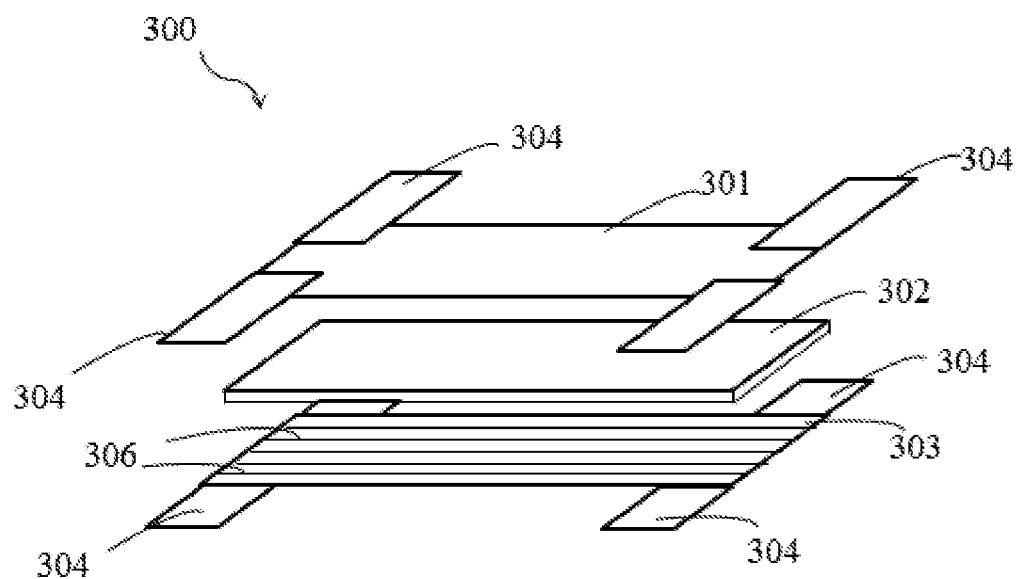
FIG. 3A is a perspective view of different layers in a diaper as per one of the embodiment of the present invention.
Figure 3B:
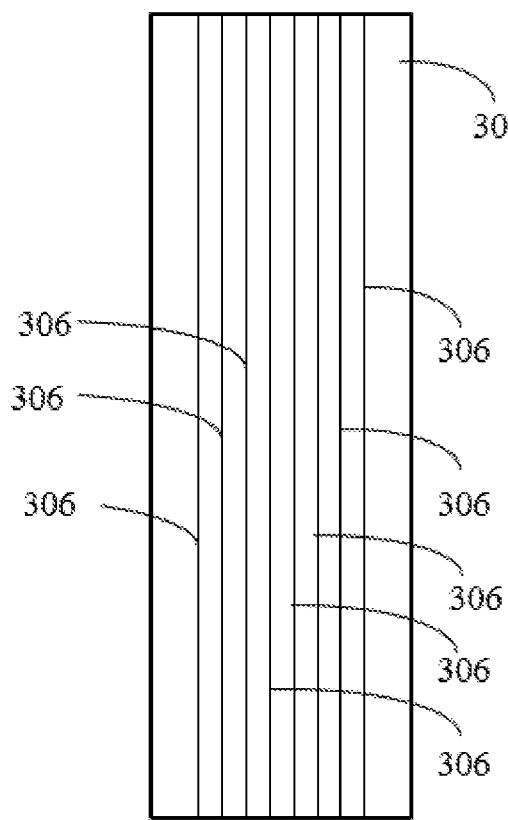
FIG. 3B is a top view of an interior side of a bottom impermeable sheet of the diaper as per one of the embodiment of the present invention.
Figure 4:
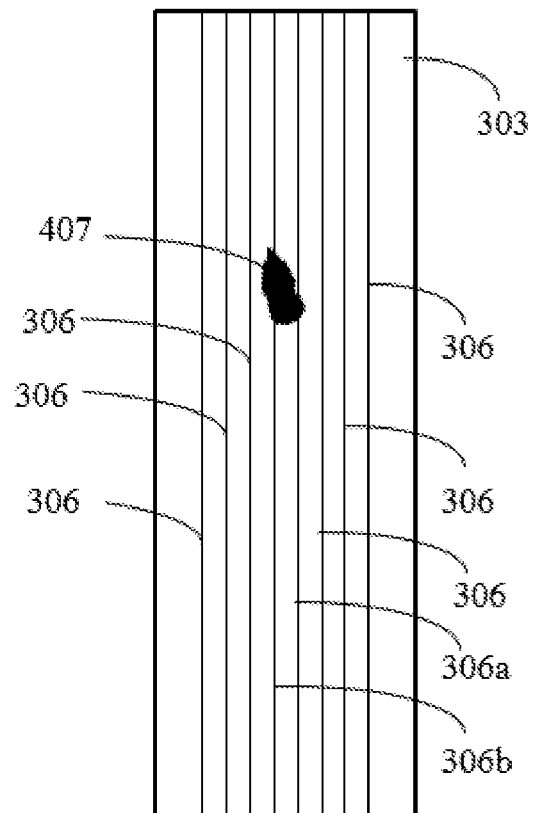
FIG. 4 is a top view of an interior side of a bottom impermeable sheet of a diaper when moisture is present as per one of the embodiment of the present invention.

To detect moisture inside the disposable diaper sensors need to be placed inside a diaper. FIG. 3A illustrates top view of diaper with sensor elements 306 present on a bottom impermeable sheet 303 of a diaper 300, as per the primary embodiment of the present invention. The diaper 300 is similar to an ordinary diaper 100 known in the art with the modification of the sensor elements 306 present on the bottom impermeable sheet. FIG. 3B illustrates a top view of the sensor elements 306 present on an interior side of an impermeable bottom sheet 303 as per the primary embodiment of the present invention. Long traces of conductive inks are sprayed on the interior side of the impermeable bottom sheet 303 and they act as the sensor elements 306. The sensor elements 306 run through the entire length of the bottom sheet 303 and are placed in such a way that the sensor elements 306 can be electrically connected to a detecting device. The detecting device provides electrical voltage to each one of the sensor elements 306. The bottom impermeable sheet 303 acts as insulators in between the sensor elements 306 as it is made up of plastic materials. Hence, no additional layer of insulating material needs to be added. When a user urinates inside the diaper 300, moisture emitted traverses through a top permeable sheet 301, and other intermediate layers (not shown) and get stored inside the absorbent pad 302, where the bottom impermeable sheet 303 act as a base and keeps the moisture from leaking. As shown in FIG. 4, the moisture 407, when it comes in contact with the bottom impermeable sheet 303, acts as a conductor between at least two sensor elements 306a and 306b. Thus the moisture 407 forms a closed circuit between at least two sensor elements 306a and 306b allowing a current to flow between the two sensor elements 306a and 306b. The detecting device can detect the closed circuit, which in turn indicates the presence of moisture. The detecting device then can generate an alert indicating presence of the moisture 407.

Figure 5:
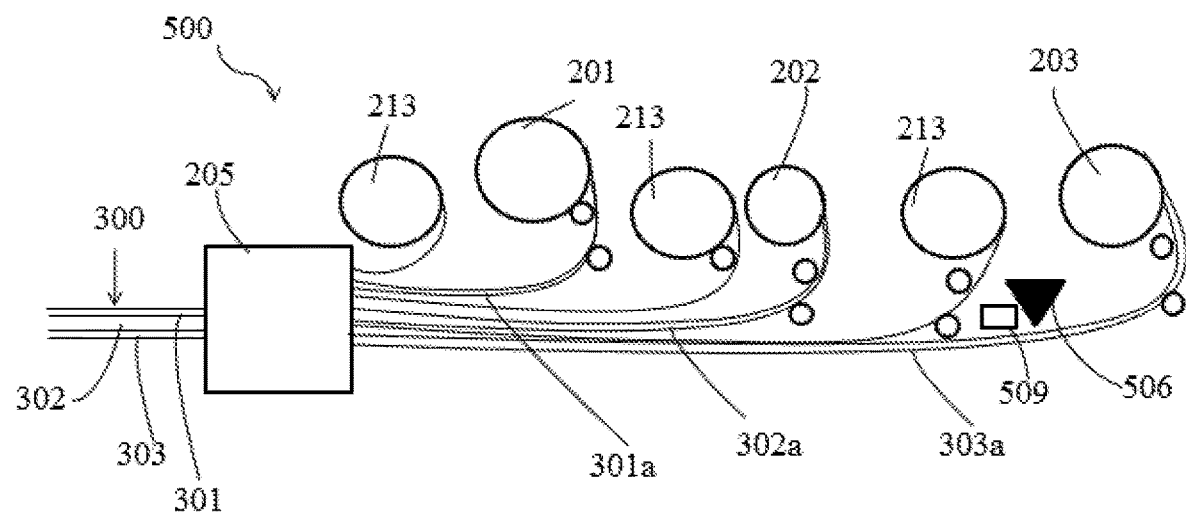
FIG. 5 is a plan view of an assembly line used for manufacturing a diaper with sensor elements as per the principal embodiment of the present invention.
Figure 6:
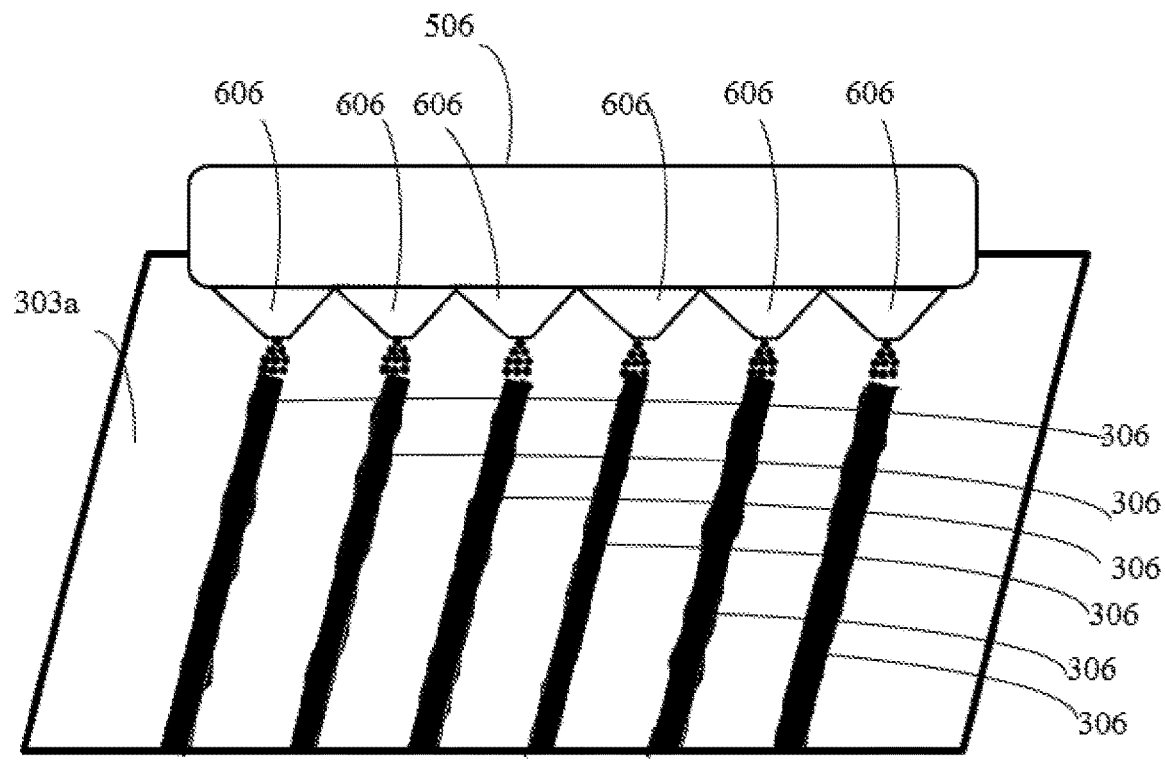
FIG. 6 is a perspective view of a sprayer drawing sensor elements as per one of the embodiments of the present invention.

FIG. 5 illustrates an assembly line 500 performing a roll-to-roll process of manufacturing the diaper 300 with sensor elements 306, as per a preferred embodiment of the present invention. The assembly line 500 is similar to the assembly line 200 described above with a small modification. A sprayer 506 is included in the assembly line 500 near the roller equipment 203 to spray conductive inks on the interior side of a sheet of an impermeable bottom sheet 303a. The sprayer 506 provides conductive inks using multiple nozzles 606 on a moving sheet of an impermeable bottom sheet 303a, as shown in FIG. 6. Movement of the sheet of the impermeable bottom sheet 303a along the assembly line 500 causes the conductive inks to form straight lines of conductive ink along the entire length of the sheet of the impermeable bottom sheet 103a. As shown in FIG. 6, the edges of the straight lines of conductive ink are not smooth as the conductive inks are sprayed. These lines of conductive inks form the sensor elements 306 that help in detecting presence of moisture inside the diaper 300. Rough edges of the sensor elements 306 does not impact the operation of the sensor elements as long as there is no connectivity between the conductive inks present on adjacent sensor elements 306. The number of sensor elements 306 that needs to be placed inside the bottom sheet 303 is directly related to the number of nozzles 606 in the sprayer 506. Right after the sprayer 506, a dryer unit 509 is attached to cure the conductive ink sprayed. The drying unit 509 can be an infra-red, laser or ultra-violet based unit also. Using a sprayer 506 to make sensor elements 306 eliminates the need of having specialized printers like ink-jet printers to print specially designed sensors on any layer of diaper material. This further reduces the time for manufacturing a diaper and also reduces the overhead of bulky printing machineries to create a sheet for a diaper that can sense moisture. Also, using the sprayer 506 eliminates the need of doing any change in the assembly line that is already in place for making disposable diapers as sprayer can be inserted at any point on an assembly line based on which layer sensor needs to be placed.

As per other embodiments of the present invention, in place of sprayer 506, other devices like pen or sketch pens can be used to draw traces of conductive inks on the interior side of the sheet of the impermeable bottom sheet 303. A single pen or sketch pen having multiple nibs can be used to draw multiple traces or multiple pens or sketch pens can be used to draw multiple sensor elements 306. The examples shown here are merely non-limiting examples while alternatives are also conceivable to a person skilled in the art. Also, it might be noted that the location of the sensor elements 306 can vary from a bottom impermeable sheet to a top impermeable sheet or any surface of the absorbent pad, depending on how and at what point a diaper manufacturer wants to detect moisture present in a diaper. Based on the location of the sensor elements 306, the location of the sprayer or pen or sketch pen and the drying unit, in an assembly line will also vary. Also, a person skilled in the art can place ink-jet printers also to print the sensing elements on any of the layers. As the sensing elements are straight lines formed mainly because of spraying of ink at stationary positions on a moving sheet of material, it reduces the task of an ink jet printer as it does not have to change the location of its print head. Thus, an ink jet printer or similar type of printers can also perform the task of spraying or printing conductive inks on any sheet of diaper in the same was as a sprayer or a pen or a sketch-pen would perform.

Figure 8B:
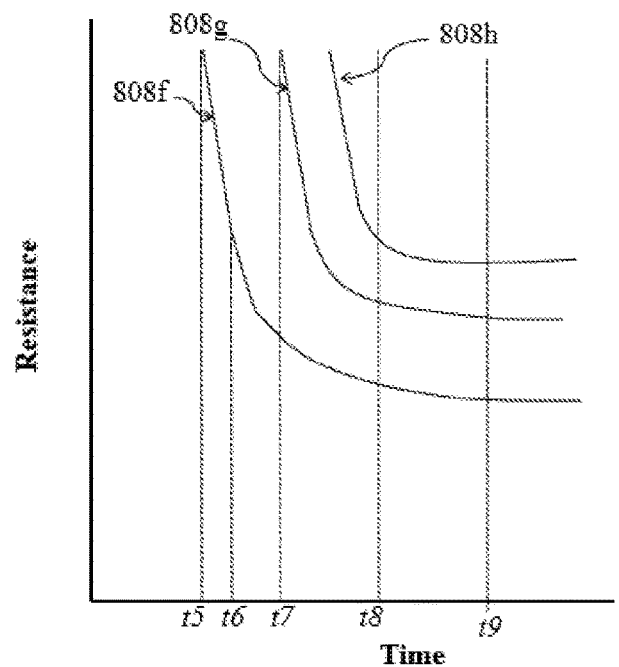
FIG. 8B is a graph depicting formation of closed circuits and their resistance with respect to time, when comparatively small volume of urine is excreted.

FIG. 7A-7D illustrates the process of detecting volume of moisture inside the diaper 300 using the sensor elements 306 present on the bottom impermeable sheet 303 of the diaper 300. As shown in the figures, when a small amount of body fluid is excreted, moisture 707 stored in the absorbent pad 302 is relatively small and it forms a closed connection between sensor elements 306a and 306b. Here, the moisture 707 can also be termed as a patch of urine. With increasing volume of body fluid, the moisture 707 will also increase and that will create more closed circuits between the sensor elements. Also, when a closed circuit is formed, a detecting device (not shown) can sense a resistance between the two sensor elements 306a and 306b. With increasing volume of moisture, resistance between the two sensor elements 306a and 306b decreases and the rate of decrease of the resistance is directly related to the rate of increase in volume of the moisture 707. Resistance will continue to decrease for every closed connection that is formed as a result of increasing volume of the moisture 707. FIG. 8A illustrates a graph of resistance of various closed circuits formed between various sensor elements 306 plotted against time. Without moisture, the resistance between various sensor elements 306 is infinity, as there is no closed connection. When user urinates, the moisture 707 of the urine creates a closed circuit and a resistance is measured for that closed circuit formed between sensor elements 306a and 306b. Gradually over time, with increasing volume of the moisture 707 due to subsequent urination, the resistance decreases to a level after which it becomes constant. This change of resistance is shown in the graph by graph trace 808a. The moisture 707 also starts spreading inside the diaper 300 and thus, another closed circuit gets formed between two new sensor elements. Resistance of that closed circuit also gradually decreases with increase in volume of the moisture 707. This decrease of resistance is shown by the graph trace 808b. Similarly, with subsequent urination, volume of moisture 707 inside the diaper 300 also increases. With increasing volume of moisture 707 over time, more closed circuits are formed and their resistances are tracked, as shown by graph traces 808c-808e. When a user is urinating inside the diaper 300, resistance of a closed circuit decreases at a fast rate for duration of time the user is urinating. After the user stops urinating, the excreted urine starts to get absorbed inside the diaper 300. When the excreted urine is getting absorbed, the resistance of the closed circuits formed decreases at a slow rate compared to earlier. Also, the detecting device can monitor how much time is required for a resistance of a closed circuit to become constant at a level. The detecting device can track amount of time required for formation of new closed circuits. This is an indication of rate at which moisture 707 is increasing inside the diaper 300. When volume of urine is more, the moisture 707 will spread more rapidly compared to when volume of urine is less. Graph shown in FIG. 8A explains the formation of closed circuits and behaviour of their resistances in details. When at first, the user starts to urinate at time t0, a first closed circuit is formed. Resistance of the first closed circuit is shown by the graph trace 808a. The resistance shown by graph trace 808a, decreases at a fast rate till time t1, after which the decrease in resistance gets slower as urine starts to spread inside the diaper 300. At time t2, urine spreading inside the diaper 300 causes formation of another closed circuit, the resistance of which is shown by graph trace 808b. Further, the number of closed circuits that are formed is dependent upon the volume of urine excreted inside the diaper 300. If a small amount of urine is excreted, the urine will cause a single or two closed circuits. If comparatively, a large volume of urine is excreted, the urine will slowly spread inside the diaper 300 causing more closed circuits, resistances of which are depicted by graph traces 808c-808e in FIG. 8A. At time t3, the urine excreted gets completely absorbed and does not spread any more inside the diaper 300. Thus, the resistances of the closed circuits become constant at their respective levels over a period of time, t4. It must be noted that level at which resistance of a closed circuit becomes constant, is directly based upon the volume of urine present between the closed circuit. When a comparatively small volume of urine is excreted, the number of closed circuits formed is also less. This is shown using graph in FIG. 8B, when the user excretes a relatively small volume of urine. Here also, from time t5 to time t6, when the user is urinating, a closed circuit is formed, resistance of which is represented by graph trace 808f. The resistance of closed circuit formed reduces at a very fast rate from time t5 to t6, when the user is urinating. After t6, the urine starts spreading inside the diaper 300 causing new closed circuits. One such closed circuit is formed at time t7, the resistance of which is shown using graph trace 808g. Before the urine gets absorbed completely inside the diaper at time t8, another closed circuit is formed, resistance of which is shown using graph trace 808h. After t8, the urine does not spread inside the diaper any more, and hence, the resistance of the closed circuits that are formed will remain constant at their respective levels for a considerable amount of time, t9. As the volume of urine excreted is less, the respective levels of resistances are also higher than compared to respective resistances when large volume of urine is excreted, shown in FIG. 8A. Further, the number of closed circuits formed in FIG. 8B is less compared to FIG. 8A, as the volume of urine is excreted is less this time compared to earlier. Thus, using the level of resistances and number of closed circuits formed, the volume of urine excreted inside the diaper 300 can be determined. A suitable alarm can be generated accordingly to give information about the volume of urine excreted.

Another factor in identifying volume of urine excreted is to track the resistance level of every closed circuit that is formed and their changes over time due to increase in volume of urine over time. When there is no urine between the sensor elements 306, there is no closed circuit and hence, resistance could not be calculated. However, when a closed circuit is formed, the resistance of the closed circuit is the total resistance of each of the sensor elements 306 plus the resistance of amount of urine causing the formation of the closed circuit. As shown in the FIG. 7A-7D, when a small volume of urine 707 is present in between sensor elements 306a and 306b, the resistance that is detected is 81 kΩ, wherein the 40 kΩ is the resistance of each of the sensor elements 306a and 306b, and 1 kΩ is the resistance of the small volume of urine 707. Now, with increasing volume of urine 707, length of the sensing elements 306a and 306b that forms the closed circuit also decreases, as shown in FIGS. 7A-7D. Resistance of a conductor is directly related to its resistivity and length, and inversely to its cross-sectional area. Thus, with increasing volume of urine 707, resistance of the closed circuit formed between sensing elements 306a and 306b decreases. The resistance of the closed circuit is tracked and from that, the length of the sensor elements 306a and 306b that is forming the closed circuit can be calculated. Thus, using resistances of all the closed circuits, the length of the sensor elements forming the closed circuits can be identified. Also, when urine starts getting absorbed inside the diaper 300, the urine spreads uniformly from a central location, causing a generally round or oval shaped patch of moisture 707. Thus, by tracking the first closed circuit that is formed and the resistance of the closed circuit, a centre of the urine can be identified. Using information about the center of the urine, number of closed circuits formed by the urine, and length of the sensor elements forming the closed circuit, the overall size of the patch of moisture 707 can be estimated. The size of the patch of moisture 707 can then be used to identify volume of urine excreted inside the diaper 300.

Further, as per another embodiment of the present invention, saturation level of the diaper 300 can be estimated based on the rate of change of resistances of the closed circuits that are formed. As described earlier, when urine spreads inside the diaper 300, new closed circuits are formed. Thus, time required for urine to spread and form a new closed circuit can be tracked. Further, as explained earlier, the resistance of the closed circuits that are formed also decreases gradually with increasing volume of urine. Hence, rate of decrease of resistances of the closed circuits and time required for formation of new closed circuits can be tracked and used to calculate absorption rate of urine in the diaper 300.

Figures 8C, 8D, 8E, 8F:
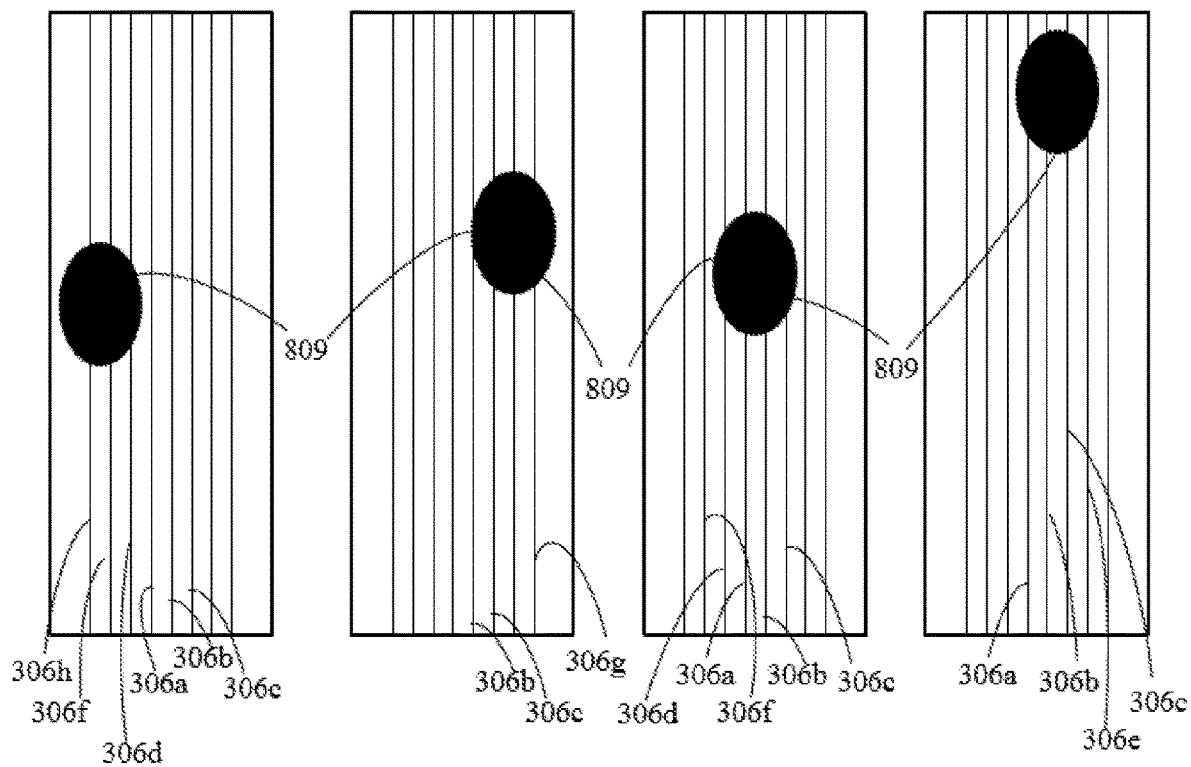
FIGS. 8C-8F is a top view of an interior side of a bottom impermeable sheet of a diaper with moisture present at different locations.

In yet another embodiment of the present invention, location of the moisture can be identified using the sensor elements 306. As shown in FIG. 8C-8F, when moisture 809 causes closed circuits between different sensor elements based on the location the moisture 809. In FIG. 8C, a closed circuit is formed between sensor elements 306h and 306d, while the other sensor elements remain in open circuit condition. In FIG. 8D, moisture 809 causes a closed circuit between sensor elements 306g and 306b. Similarly, FIGS. 8E and 8F shows different location of moisture 809 and different sensor elements that gets connected in closed circuits as a result of the moisture 809. The detecting device can be programmed to generate different types of alert that provides information about different location of the moisture. Also, based on the location of moisture, current absorption rate of urine in the diaper 300 and the time required to form new closed circuits, the detecting device can predict the volume of urine in the diaper 300. Thus, a suitable alarm can be generated.

In yet another embodiment of the present invention, the sensor elements 306 can be used to identify when the diaper 300 is about to get saturated. The sensor elements 306 runs along the entire length of the impermeable bottom sheet 303, and the detecting device can identify how many closed circuits are formed by the moisture present inside the diaper. When a user excretes inside the diaper, in general, moisture at first remains at the central portion of the diaper and slowly with increasing volume of excretion, moisture spreads to edge portions of the diaper. When closed circuits are formed between the sensor elements 306g and 306h present in the edges of the impermeable bottom sheet 303, as shown in FIG. 7D, the detecting device can identify that moisture has reached the edges. The resistance of all the closed circuits will continue to decrease with more and more urine spreading inside the diaper 300. Combining the information about the resistance and number of closed circuits formed, and the closed circuit formed between sensor elements 306g and 306h, the detecting device can predict that the diaper 300 is about to reach saturation. The detecting device can generate an appropriate alert indicating that the diaper 300 is about to reach saturation.

Figure 8G:
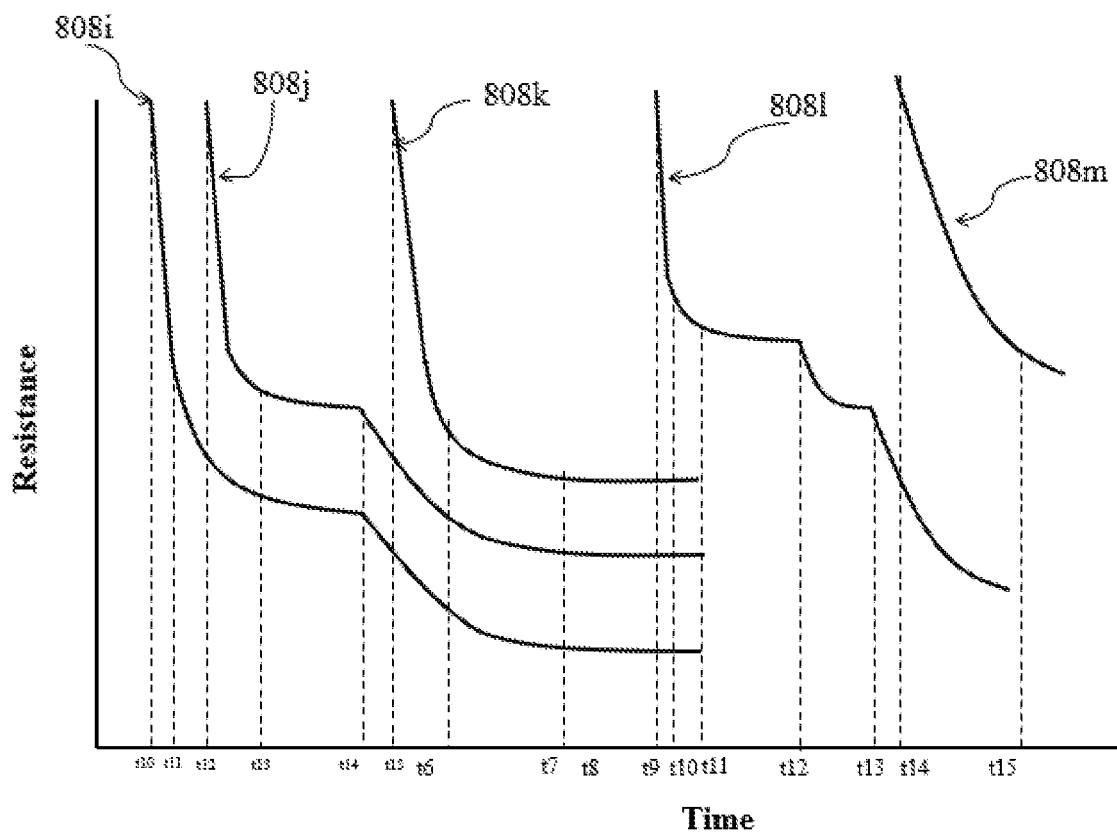
FIG. 8G is a graph depicting formation of closed circuits with their resistance when urine is excreted multiple times.

FIG. 8G illustrates behaviour of resistances of closed circuits in the diaper 300 with sensing elements 306 present on the bottom impermeable sheet 303, when a user urinates multiple times. At first, when starts urinating at time t10, a closed circuit is formed, the resistance of which is depicted by graph trace 808i. Between time t10 to time t11, when the user is urinating, the resistance of the closed circuit that is formed reduces rapidly. After t11, the urine starts spreading inside the diaper 300 causing a new closed circuit at time t12, while the resistance of the already formed closed circuit starts to reduce gradually. Resistance of the new closed circuit is depicted using graph trace 808j. When the urine gets completely absorbed inside the diaper 300 and stops spreading, the resistances of the closed circuits becomes constant. As explained in the previous embodiments, the number of closed circuits that are formed, and level at which their respective resistances becomes constant, are directly related to the volume of urine excreted by the user. The resistances remain more or less at their respective constant levels till the time, the user starts urinating again at time t14. AT time t14, resistances of the already formed closed circuit starts to reduce rapidly till the time, the user continues to urinate. At time t15, another closed circuit is formed, the resistance of which is depicted by graph trace 808k. The resistances of all the closed circuits will continue to decrease rapidly till time t16, when user stops urinating. After time t16, the urine starts getting absorbed and stops spreading at time t17, after which resistances of all the closed circuits becomes constant at their respective levels. As mentioned earlier, using the resistance level of all the closed circuits, and center of urination, the overall volume of urine present in the diaper 300 can be estimated.

Figure 9A:
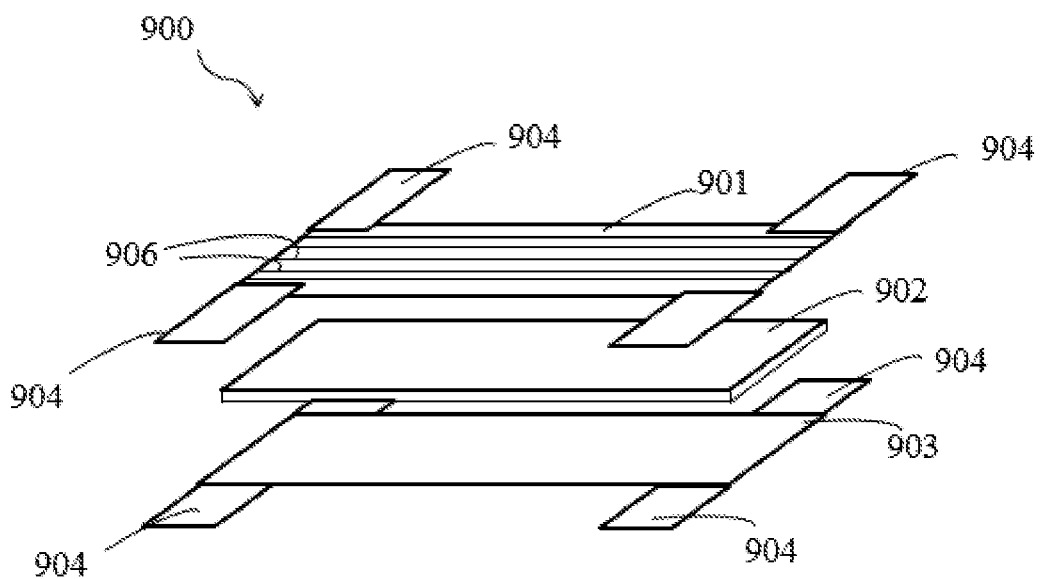
FIG. 9A is a perspective view of different layers in a diaper as per another embodiment of the present invention.
Figure 9B:
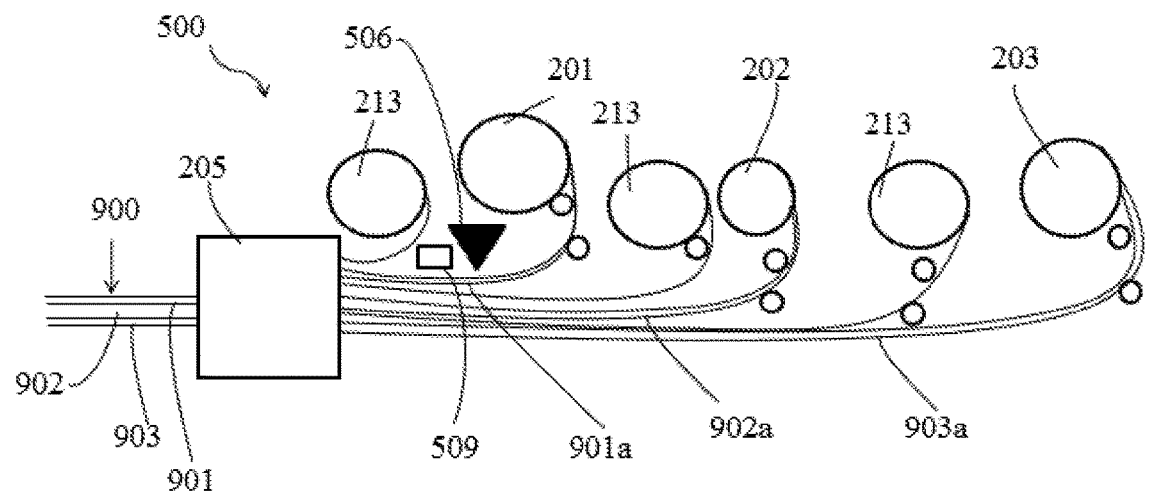
FIG. 9B is a plan view of an assembly line used for manufacturing a diaper with sensor elements as per the embodiment of the present invention.

FIG. 9A-9B illustrates a diaper 900 with sensing elements 906 present on a top permeable sheet 901 and a process of manufacturing it as per another embodiment of the present invention. The sensing elements 906 are made using the sprayer 506 placed near roller equipment 201 providing top permeable sheet 901a in an assembly line 500. Right after the sprayer 506, a dryer unit 509 is also attached to cure the conductive ink sprayed. The drying unit 509 can be infrared, laser or ultra-violet based unit also. The assembly line used in the embodiment is similar in operation as that of the assembly line 500 described in previous embodiments. The sensing elements 906 formed on top of the top permeable sheet 901 are similar in shape and design as described in the previous embodiments. The top permeable sheet 901 acts as in insulator between any two sensing elements 906 that maintains an open circuit between two adjacent sensing elements 906, when the diaper 900 is dry. However, sensing elements can also be placed on a bottom surface of the top permeable sheet 901 by changing the location of the sprayer 506. The sensing elements 906 as described in the previous embodiments, run parallel to each other along an entire stretch of the top permeable sheet 901 and are connected to a detecting device, which is similar in operation as mentioned in the previous embodiments. Also, it must be noted that any person ordinary skilled in the art can place the sensing elements as per the present invention on any one of the intermediate layers inside the diaper or on top of the top permeable sheet 901, by changing the position of the sprayer 506 in an assembly line used for manufacturing a diaper.

The operation of the sensing elements 906 is similar to the operation of the sensing elements described in previous embodiments. However, formation of closed circuits and change of resistance will be different from the previous embodiments as the location of the sensing elements varies. When a user urinates inside the diaper 900, the urine forms a closed circuit between at least any two of the sensing elements 906. When, the absorbent pad 902 soaks in the urine, the closed circuit will be broken. As a result, the detecting device will sense a fall in resistance between any two sensing elements 906 for a short amount of time and then again, the resistance will rise. When the user urinates again inside the diaper 900, a closed circuit is again formed between at least any two of the sensing elements 906. This closed circuit will also, remain for an amount of time till the absorbent pad 902 soaks in the moisture again. Thus, with more and more urine being excreted, rate of absorption of the absorbent pad 902 will also starts to decrease and the pad will starts to reach saturation level. As a result, closed circuits formed between any two sensing elements 906 will remain for a longer amount of time with increasing saturation level of the absorbent pad 902. This is explained using graph shown in FIG. 10.

Figure 10:
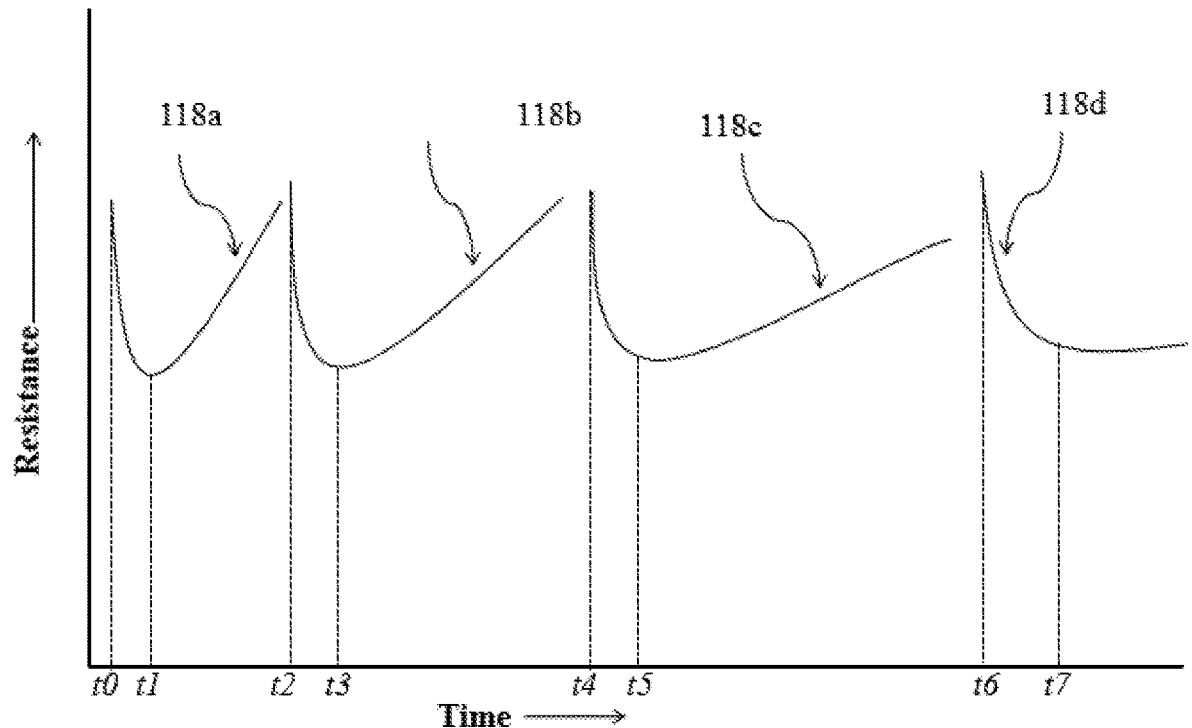
FIG. 10 is a graph depicting formation of closed circuit and their resistance with respect to time as per the another embodiment of the present invention.

FIG. 10 shows change of resistance in between sensing elements 906, present on the top permeable sheet 901 of the diaper 900, as detected by the detecting device. At first, when a user urinates, at least a closed circuit is formed between two adjacent sensing elements 906. The detecting device can detect a resistance between those two sensing elements. Slowly, the urine gets soaked inside the absorbent pad 902 and the closed circuit becomes open. Thus, resistance detected by the detecting device will again start to increase with more and more urine being soaked in, till it becomes infinite. Please note that sometimes, a closed circuit may remain because of the retained moisture. This is shown in FIG. 10 using graph trace 118a. The time during which, resistance of a closed circuit decreases very sharply can be called as an urination event. Time t0 to time t1 in FIG. 10, is the time a user urinates, during which with more and more urine being discharged, the resistance between the two elements starts to decrease. After t1, with increasing volume of urine getting soaked inside, the resistance starts to decrease till all the urine gets soaked in and the circuit becomes open circuit again. When the user urinates again, another closed circuit will be formed between the earlier adjacent sensing elements or new pair of sensing elements. This closed circuit will again go through a similar cycle of resistance increase between time t2 and t3, when the user is urinating and subsequent decrease of resistance after time t3, as shown in FIG. 10. With every subsequent urination event, speed in which urine will be soaked inside the absorbent pad 902 will be slower. Hence, the closed circuit formed now will remain for much longer duration. This is shown using graph trace 118b. With more urination inside the diaper 900, time required by the absorbent pad 902 to soak in urine will increase and hence, closed circuits formed by the urine will remain for longer duration. This is shown by graph trace 118c, where the user urinates from time t4 to time t5. After t5, the urine starts to get soaked inside and hence, resistance starts to decrease. Finally, a time will come when the absorbent pad is almost saturated and could not soak in more urine. The closed circuit formed then will remain for a much larger duration of time. Hence, the resistance will rise very slowly. This is shown using graph trace 118d, where the user urinates from time t6 till time t7. After time t7, the urine will get absorbed slowly and as a result, the resistance rises back at a very slow rate. If the resistance rise back less than a predetermined threshold over a predetermined time t8, then the detecting device can generate an alarm. The detecting device can also generate alarms at different threshold levels to indicate whether the diaper 900 is about to reach saturation or is already saturated. In another aspect of the present invention, time required to absorb urine and number of closed circuits formed, can be used to detect volume of urine excreted inside the diaper. The detecting device can be programmed to generate different type of alarms based on different volume of urine detected.

It must be noted that the sensing elements can be sprayed on any one of the intermediate layers also and basis where the intermediate layers are located, the detecting device can process resistance information in different ways to detect the saturation level of the diaper, volume of the urine inside the diaper and also the location of urine. The process of spraying the sensor elements on any of the intermediate layers remains same as the previous embodiments and can be easily achieved by changing the location of the sprayer in the assembly line for manufacturing diaper. A person skilled in the art can also spray the sensing elements on any surface of the absorbent pad easily by placing the sprayer near the roller equipment supplying sheet of absorbent pad on the assembly line for manufacturing diaper. Further, it must be noted that based on the location of the sensing elements inside the diaper, the detecting device must be programmed accordingly to process resistance information coming from the sensing elements. Also, it is imperative that the sensing elements should be designed in such a way that they get electrically coupled to the detecting device.

Figure 11:
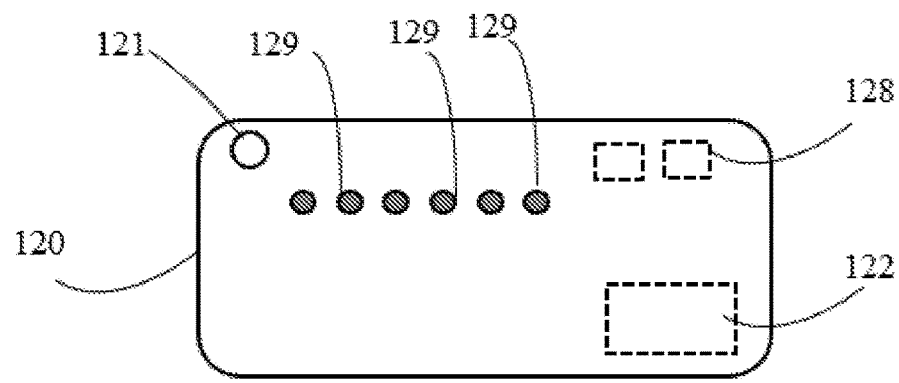
FIG. 11 is a portable detecting device as per one of the embodiments.

Referring to FIG. 11 now, a detecting device 120 made up of insulating material is shown. The detecting device 120 has contact points 129 which are used to connect to the sensor elements that are present on a diaper as per the present invention. The contact points 129 is made up of conducting materials as they couple the sensor elements to processing components 128 present inside the detecting device 120. Also, it might be noted that the number of contacts points 129 should be same as the number of the sensor elements. The detecting device 120 is adapted to receive and process closed circuit information picked up through the sensor elements and subsequently, analyse resistance information of the closed circuits to identify presence of body fluid and volume of body fluid inside the diaper. The detecting device 120 can then generate an alert or the like by wireless or wired means. For example, the alert may include sending a text message to a caretaker's cell phone with information about the degree of wetness and the location(s) of wetness on a diaper. The detecting device 120 is also capable of generating a visible or an audible alert signal through its inbuilt indicator/s 121. In that case, the alert may also be a visual or an audible alert generated by in-built indicators 121, indicating the amount of body fluid excreted and when the diaper needs to be changed. The battery 122 present in the portable detecting device 120, provides electric power to the processing components 128, as well as supplies power to the sensor elements. The portable detecting device 120 is designed to be attached to either the bottom impermeable sheet or the top permeable sheet of the diaper, using multiple techniques including clamping or adhesive or mechanical based fastening products or snap lid or by wrapping around the extended portions of the bottom impermeable sheet or extended portions of the top permeable sheet.

Figure 12A:
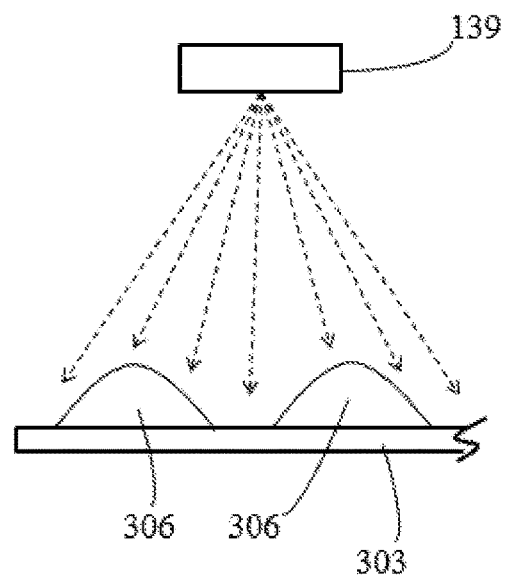
FIGS. 12A-12B are cross sectional views of a section of bottom impermeable layer with an infra-red based drying unit used to dry the sensor elements.
Figure 12B:
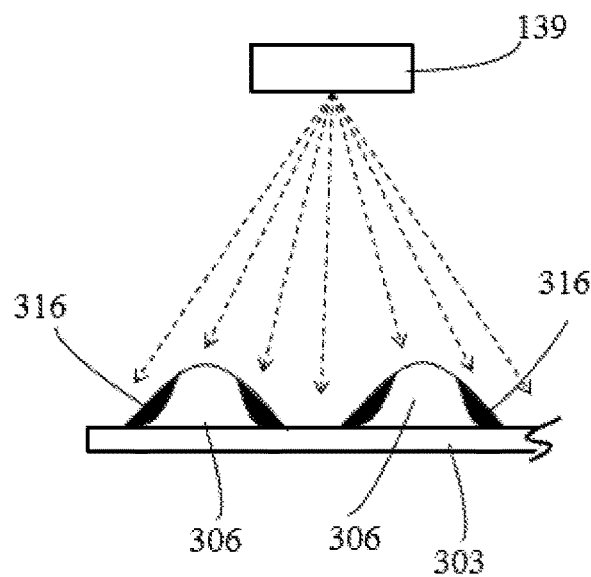

As shown in the above embodiments, the sensing elements are created by spraying conductive inks on a rolling sheet of either a top permeable layer or a bottom impermeable layer of a diaper. The conductive inks sprayed on a bottom impermeable layer needs to dried before other layers can be placed on top of it. Otherwise, there is a possibility that the conductive inks may leech into other layers when other layers of diaper contact the bottom permeable layer. Same is true for conductive inks sprayed on top permeable layer. To eliminate the possibility of conductive inks leeching into other layers, a drying unit is used right after a sprayer in an assembly line for manufacturing diapers, as explained in the previous embodiments. FIG. 12A-12B, show a cross sectional view of a section of bottom impermeable layer 303 with an infra-red based drying unit 139 in an assembly line for manufacturing diapers as per one of the embodiment of the present invention. The material of the bottom impermeable layer 303 of any diaper is made up of plastic that is invisible to infra-red rays and hence, infra-red based dryers can be used to dry conductive inks without causing any effect on the bottom impermeable layer 303. As shown in FIG. 12A, conductive inks that are sprayed on the bottom impermeable layer 303 form a straight sensing element 306 with more ink at a central portion compared to edge portions. The sensing element 306 formed has shape similar to a series of ink drops on the bottom impermeable layer 303. When the sensing elements 306 get exposed to the infra-red rays emitted from the drying unit 139, the ink starts to get dried up or cured. However, infra-red rays need a lot of time for curing the conductive inks. An average speed of the assembly line is around 5 m/sec and thus, the conductive ink do not get enough exposure to the infra-red rays to get completely cured. As a result, surface area of the conductive ink that are near the edge portions, where the thickness of ink is less, gets cured, whereas the central portion remains uncured, as shown in FIG. 12B. Thus, when another diaper layer is placed on top of the bottom impermeable layer 303, the risk of leeching of conductive ink still remains. One way to counter the risk is to have high volume of infra-red rays, which would increase the cost of the drying unit 139. Another possible solution is to slow down the assembly line so that the conductive ink can be exposed to the infra-red radiation for a longer duration of time. As evident, slowing the assembly line would cause huge loss of operational costs and will also be inefficient.

Figure 13A:
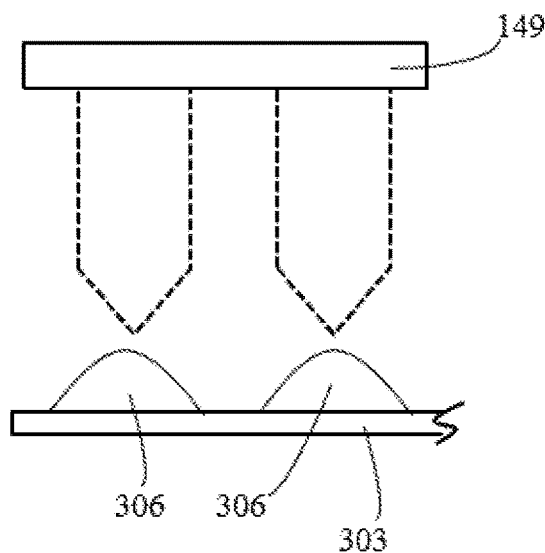
FIGS. 13A-13B are cross sectional views of a section of bottom impermeable layer with a laser based drying unit used to dry the sensor elements.
Figure 13B:
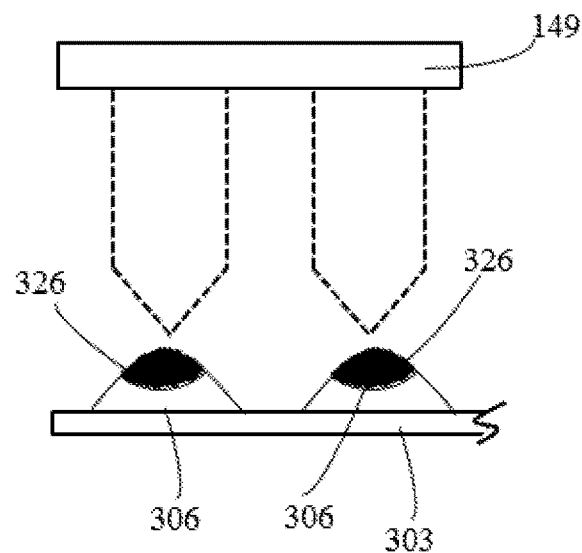

A possible way to reduce the risk of leeching on conductive ink is to use laser based drying unit as shown in the FIG. 13A-B. As per this embodiment, a laser based drying unit 149 is used to direct laser rays directly on top of a the sensing elements 306 present on top of the moving bottom impermeable layer 303. Laser radiations causes outside surface of the central portion of the sensing elements 306 to get cured faster and thus forming a crusty solid outer surface 326 at the top as shown in FIG. 13B. The crusty solid outer surface 326 of the sensing elements 306 allows other diaper layers to be placed on top of the bottom impermeable layer 303, without the risk of conductive inks leeching into the other diaper layers. The laser also generates more heat which causes shrinkage of the conductive inks and thus, the conductive inks present on the edge portions of the sending elements 306, does not leeches into any other diaper layer that is placed on top of the bottom impermeable layer 303. Thus, using laser based drying unit 149, the curing of the conductive inks can be done efficiently and effectively. Also, it must be noted that the same curing technique can also be used to cure conductive inks sprayed on a top permeable layer of a diaper with similar affects.

Figure 14:
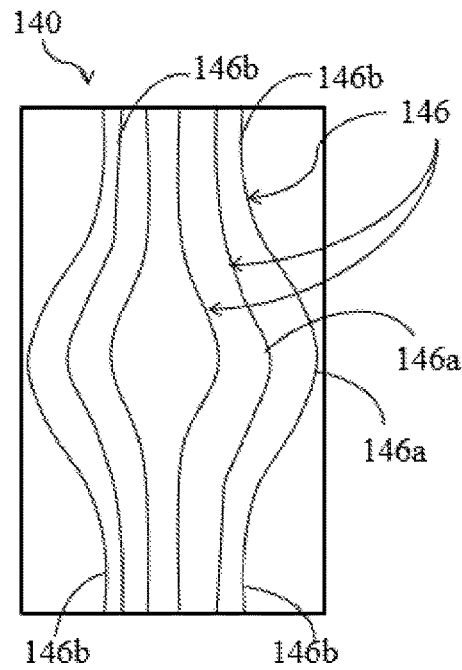
FIG. 14 is a top view of a sheet of diaper with curved sensor elements.

In yet another embodiment of the present invention, sensor elements are designed in such a way that they form a curve at a central portion of a diaper. As shown in FIG. 14, curved sensor elements 146 have curves 146a, such that the curves 146a lie at a central portion of a diaper 140. Generally, the central portion of the diaper 140 is the portion at the bottom of a wearer, where maximum urine gets stored. As a result, the urine will spread more width-wise at the central portion of the diaper 140. To identify extent of how much urine has spread at the central portion, linear sensing elements need to be present throughout the entire width of the diaper 140. As a result, the linear sensing elements present along the entire width of diaper will need a very big detecting device to have contact with all the linear sensing elements. A big detecting device will cause problems in connecting the device properly with all the sensor elements.

Also, it will be uncomfortable for a wearer to move around with a big detecting device attached to the diaper 140. Having curved sensor elements 146 with curves 146a solve the problem by having increased detection area at the central portion of the diaper 140 and reduced contact area for a detecting device. As shown in the FIG. 14, curves 146a of the curved sensor elements 146 can reach up to entire width of the diaper 140 at its central portion. Hence, an increased detection area is achieved at the central portion of the diaper 140. Further, with the curves 146a, present only at the central portion, the curved sensor elements 146 forms contact portions 146b placed within a very small area. Having contact portions 146b placed within a very small area reduces size of the detecting device that is required to be connected to the curved sensor elements 146. Also, it must be noted that the curved sensor elements 146 with curves 146a can be present on either a bottom impermeable layer or a top permeable layer or both, of the diaper 140, based on the manufacturer and detection algorithms used by the detecting device.

Figures 15A, 15B, 15C:
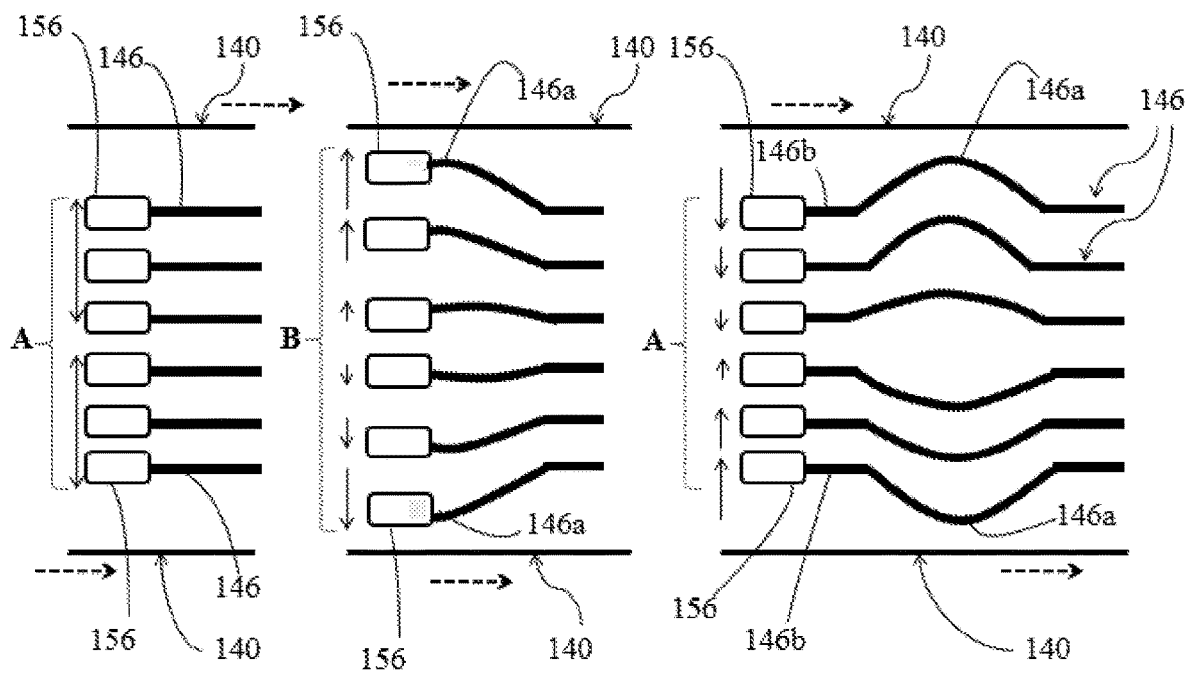
FIGS. 15A-15C are plan views of a manufacturing process of a sheet of diaper with curved sensor elements.

FIGS. 15A-15C describes a method of manufacturing a diaper layer with curved sensor elements 146. Please note that the diaper layer can be any layer of the diaper 146 upon which conductive ink can be sprayed upon to create sensor elements. As shown in FIG. 15A, multiple nozzles 156 spraying conductive inks on a moving layer the diaper 140, create sensing elements 146 on the layer of the diaper 140. The direction of movement of the layer of the diaper 140 is shown using dotted arrows in FIGS. 15A-15C. As explained in previous embodiments, spraying of conductive inks on a moving layer of the diaper 140 causes formation of sensing elements on that layer. To create curved sensing elements 146, the nozzles 156 are designed in such a way that they can move in tandem in directions perpendicular to the direction of movement of the moving layer of the diaper 140. Arrows in FIG. 15A depicts directions in which the nozzles 156 can move from their primary position A. When each nozzle is moved while it is spraying conductive inks on a layer of the diaper 140, due to the movement of the layer of the diaper 140, each of the sensing elements 146 also starts to deviate from their linear design and start forming curves. As depicted in FIG. 15B, different nozzles move in directions shown by arrows, and reach a position B, which leads to formation of first half of curves 146a of the curved sensing elements 146. Further, as depicted by the arrows, different nozzles 156 move different distances to reach position B. The different distances are predetermined based on the width of the diaper 140, such that the curves 146a that are formed covers maximum area of the width of the diaper 140. If the diaper 140 have a small width, nozzles 156 need to be moved less to create a curve that can cover maximum area of the width of the diaper 140. In case the width of a diaper 140 is more, to create a curve having similar feature will require more movement for the nozzles 156. Also, the speed at which the nozzles 156 are moved is predetermined based on speed of the moving layer of the diaper 140. Both the speed and distance of movement of the nozzles 156 are predetermined so as to create curves 146a that covers maximum area at the central portion of the diaper 140. From position B, the nozzles 156 are moved back to their initial position A, so as to create second half of the curves 146a, as shown in FIG. 15C. After reaching the initial position A, the nozzles are kept at that position for a predetermined time to so as to create contact portions 146b placed within a very small area. Thus, a layer of diaper 140 is manufactured having curved sensing elements 146, such that the sensing elements 146 cover a maximum area at a central portion of the diaper 140. The process is repeated multiple times to create a moving sheet of the layer of diaper 140 from which multiple diapers 140 can be cut out. Further, the curves 146a can be of any shape, as long as the sensing elements 146 do not overlap each other. Different shapes of the curves 146a can be achieved by varying the distance of the movement and speed of movement of the nozzles 156.

Also, it must be noted that along with the nozzles 156, drying units also has to move in accordance with the nozzles 156, so to efficiently dry the conductive inks forming the curved sensing elements 146. Further, in place of all the nozzles moving, separate spraying units can also be deployed wherein each individual spraying unit is moved rather than the nozzles 156. Other similar arrangements can be made based upon whether the spraying unit is a pen, sketch pen or similar means used for drawing or spraying sensor elements on a moving sheet of diaper.

Figure 16A:
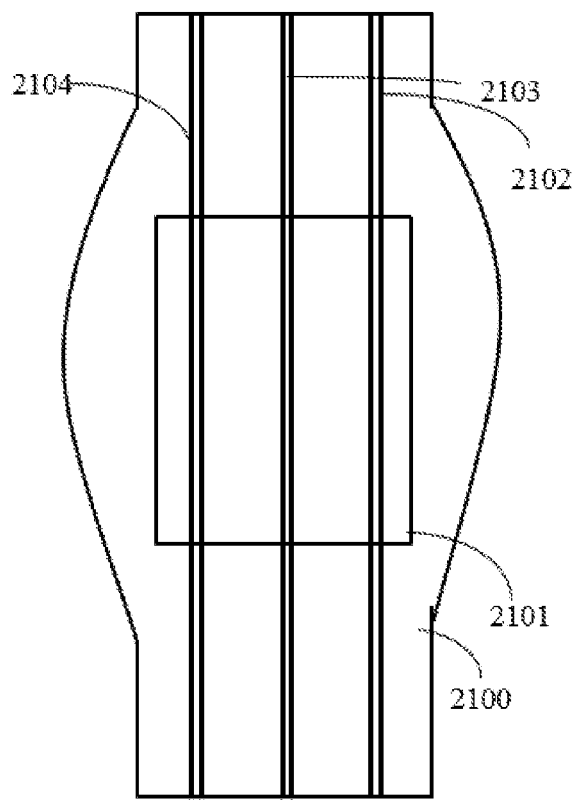
FIG. 16A illustrate a top view of a bottom layer with new embodiment of the present invention.

In yet another embodiment of the present invention, multiple sensing elements are grouped together in pairs and placed on the bottom layer of a diaper. FIG. 16A illustrates a bottom layer 2100 of a diaper with pairs 2104, 2102, 2103 of electrodes running the entire length of the diaper and spread across the width of the diaper. The pairs of sensing electrodes is sprayed on the bottom layer 2100 using sprayers as mentioned in the previous embodiments of the present invention. As per one of the primary embodiments of the present invention, the sensing electrodes are pre-printed on the bottom layer 2100 using any method known in the art. The primary utility of this embodiment of the present invention is that the sensing elements are present before assembling various layers of the diaper without the need of a cutting device registering the pattern of the sensing electrodes. In most diapers, an absorbent pad (not shown) is present in the middle section 2101 of the diaper. As per this embodiment of the diaper, sensing elements paired in pairs that run across the entire length of the diaper. The pair 2103 is present at or near the center of the bottom layer 2100 and facing the absorbent pad placed on top of it. Two more pairs 2102 and 2104 are placed at or near or close to two edges of the section 2101 and run through the entire length of the diaper. The pairs 2102 and 2104 are chosen to be placed as close as possible two the two edges of the section 2101. The pair 2103 is used to detect presence of urine whereas the pairs 2102 and 2104 are used to detect the spreading of urine, which in turn is used to detect saturation of the diaper. All the pairs are connected to a detecting device that provides electrical signals through the sensing electrodes. The detecting device has the same functionality as that of the detecting devices described in the previous embodiments of the present invention.

Figure 16B:
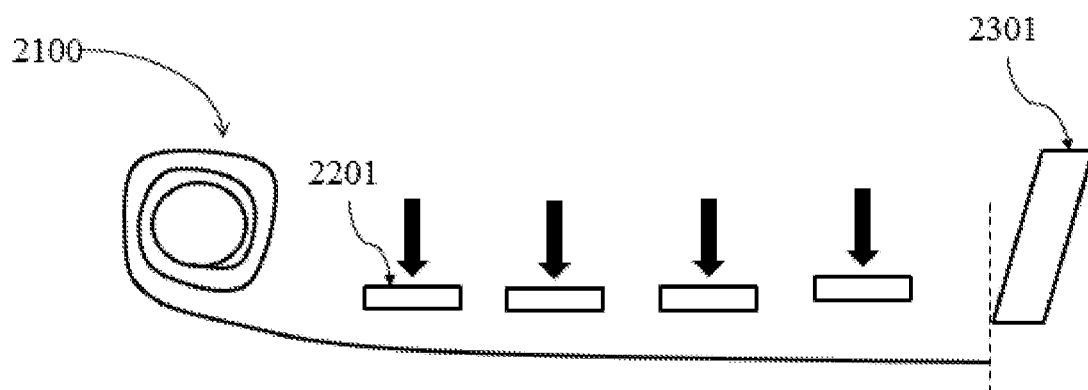
FIG. 16B illustrate a method of manufacturing a diaper as per the new embodiment of the present invention.

FIG. 16B explains the process of installation and cutting of the bottom layer 2100 of a diaper after installing absorbent pad 2201. The absorbent pads 2201 are installed on a rolling sheet of bottom layer 2100 on sequential basis. Other layers of diaper could be placed on top of the absorbent pads 2201. The sheet 2100 is then passed to a cutting machine 2301 which cuts the sheet 2100 into different diaper sections. The sheet 2100 is pre-printed with pair of sensing electrodes as explained earlier. The advantage of having pre-printed sensing electrode pairs as per this embodiment is that the cutting machine 2301 can cut it at any location and yet a detecting element can detect the moisture inside that diaper using the sensing elements. Previously, the cutting machine 2301 has to cut a diaper at predefined positions for a detecting device to get connected to the sensing electrodes.

Figures 17A, 17B:
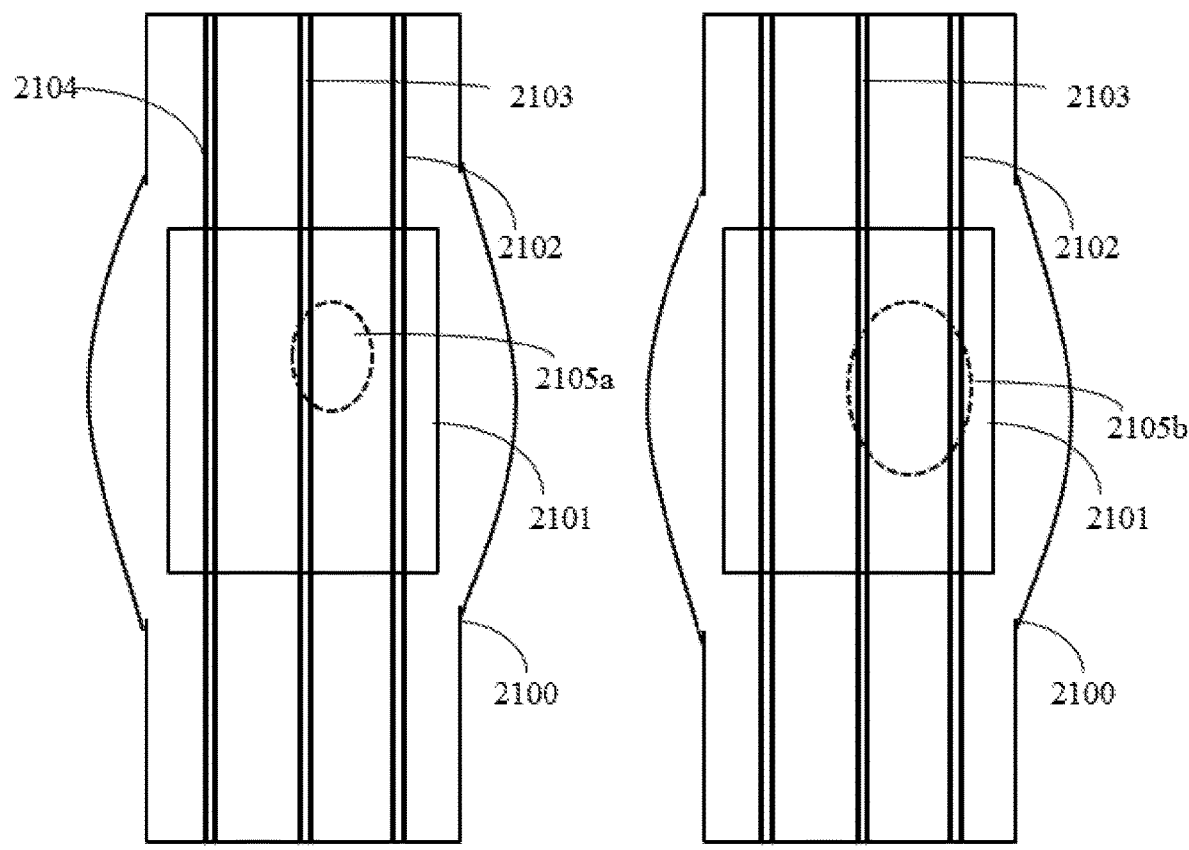
FIGS. 17A-17B illustrates a method of detecting moisture present in the moisture inside the diaper as per the new embodiment of the present invention.

FIG. 17A-17B illustrates detection of urine using the pairs of sensing electrode. In FIG. 17A, urine 2105a is present on the absorbent pad. The urine 2105a will cause a closed a circuit between sensing electrodes of the pair 2103, indicating presence of urine in the central portion of the absorbent pad. With increasing volume of urine 2105a, the urine increases to 2105b causing a closed circuit between sensing electrodes of pair 2102. The formation of closed circuit between 2103 and then 2102 shows increase of urine inside the diaper and also the area at which the urine is increasing. Since, urine will be present at first at the central portion, the first closed circuit that will be formed will be between pairs 2103. With increasing urine, the conductance between the formed closed circuits also increases. The second closed circuit will be either or both of the pairs 2102 and 2104, indicating that urine has reached the edges of the absorbent pad. Based on the exact location of the pairs 2102 and 2104, the saturation level of the absorbent pad could be predicted.

In scenarios where closed circuit is formed between both the pairs 2102 and 2104, conductance of the closed circuit 2103 could be measured to know the exact volume of the urine. Similarly, when one of the 2102 and 2104 have a closed circuit, this indicates that urine is located on that side of the absorbent pad and with further increase, might leak on that side of the diaper. Based on the situation different alarms could be programmed to be emitted by the sensor device.

Figure 18A:
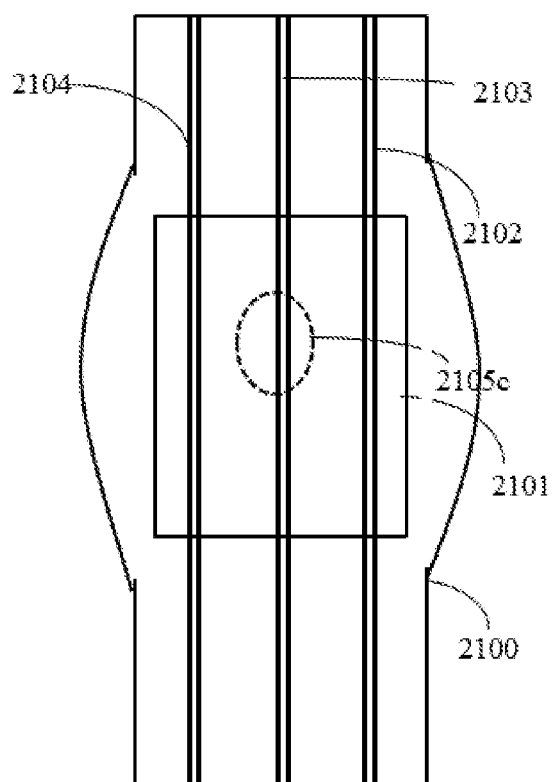
FIGS. 18A-18E describe various closed circuit formed by moisture inside the diaper as per the new embodiment of the present invention.
Figure 18B:
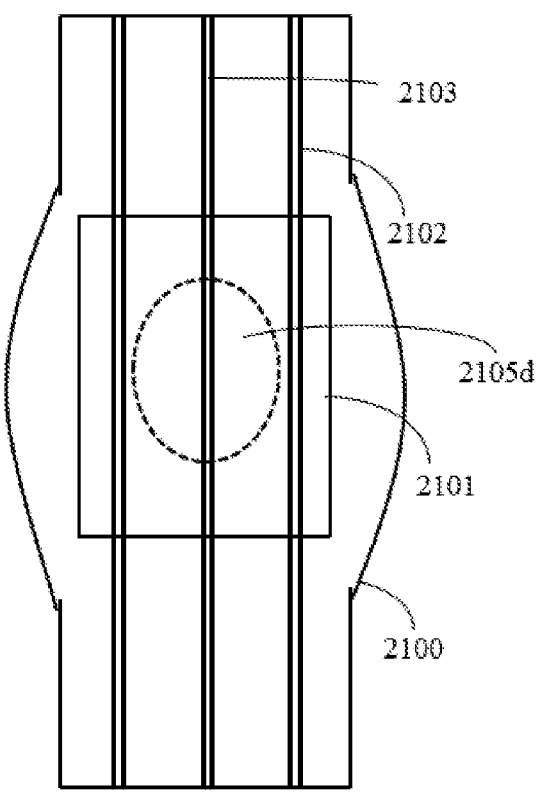
Figure 18C:
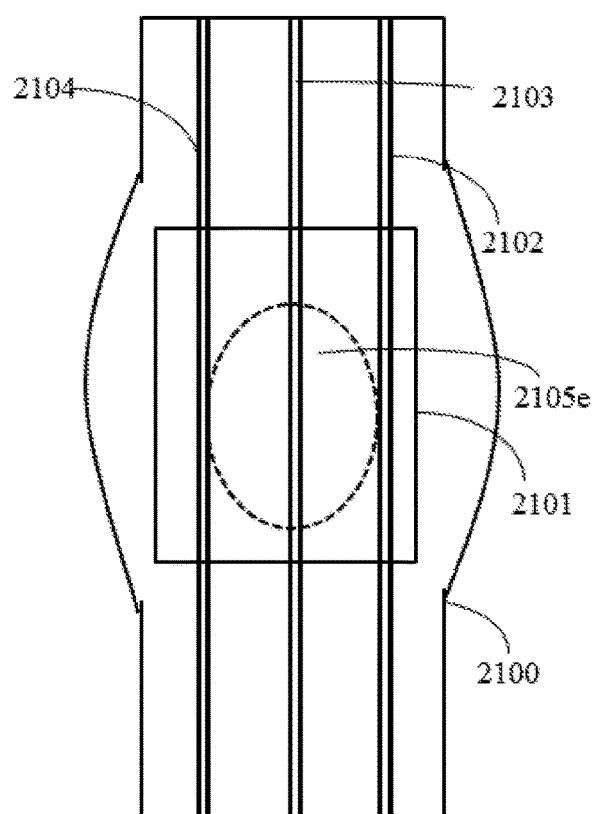
Figure 18D:
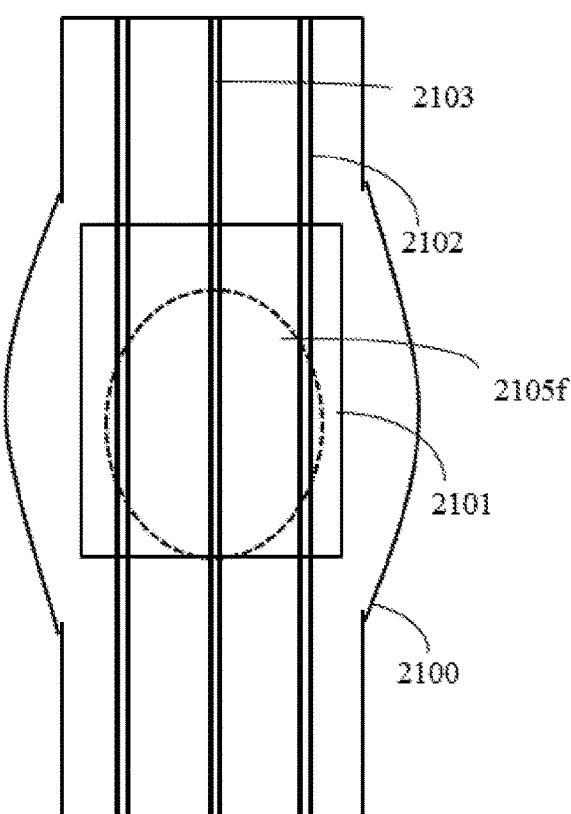

FIG. 18A-18C illustrates expansion of urine inside a diaper with sensing electrodes pair present in the bottom layer. When urine is first present inside the diaper, the absorbent pad soaks in the diaper and stores it. This urine creates a patch of moisture 2105c in the central portion 2102 of the bottom layer 2100. The patch 2105c creates a closed circuit between sensing electrodes of the pair 2103 as illustrated in FIG. 18A. With increasing volume of urine inside the diaper, the patch increased to size 2105d as shown in FIG. 18B. Since, the moisture patch 2105d do not touch any one of the pairs 2102 and 2104. Thus, no closed circuit is formed. When urine further increases inside the diaper, the volume of the patch 2105e increases and just touches one of the sensing electrodes of the pairs 2102 and 2104. Thus, closed circuit is not formed between the sensing electrodes of any one of the pairs 2102 and 2104. As per yet another embodiment of the present invention, each individual sensing electrode is connected to one or multiple individual sensing electrode of another pair through the detecting device. Thus, as per one embodiment of the present invention, the moisture patch 2105e could be detected because it forms a closed circuit between one sensing electrode of pair 2102 and one sensing electrode of pair 2104. This is explained further using FIG. 18E. With further increase of urine inside the diaper, the moisture patch 2105f creates closed circuit between both or either once of the pairs 2102 and 2104. The closed circuits formed between the sensing electrodes of the pairs 2102 or 2104 indicates that the urine has reached the edges of the absorbent pad. Thus, suitable alarm could be raised to indicate the amount of urine present inside the diaper or could be used to calculate the saturation level of the diaper.

Figure 18E:
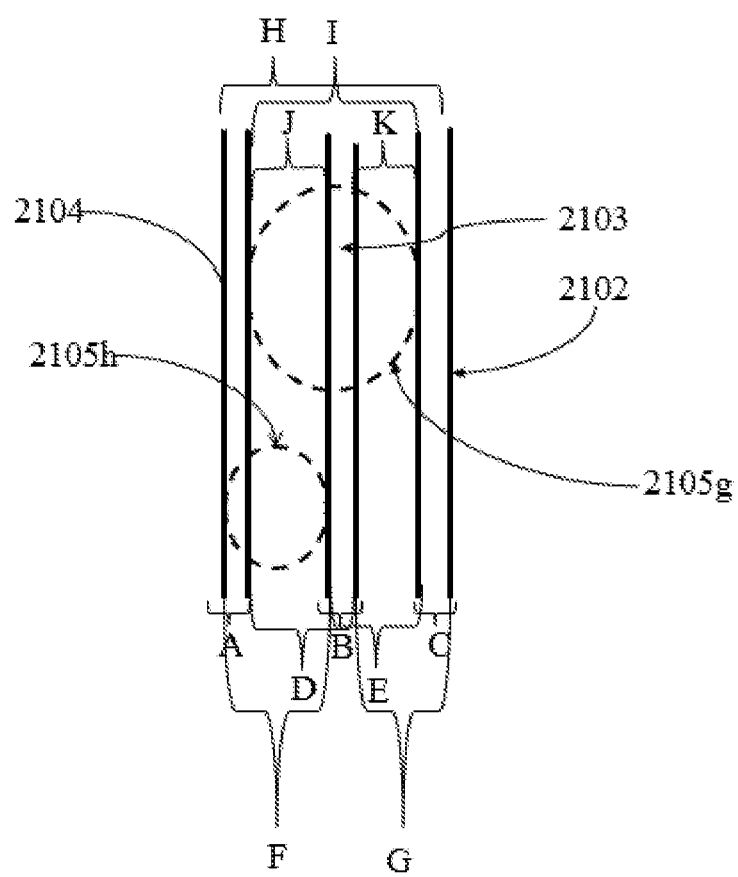

FIG. 18E illustrates various closed circuit that could be formed by urine present inside a diaper. As per this embodiment, all the single electrode of pairs 2102, 2103 and 2104 are connected to each other and hence, the detecting device can detect closed circuit formed between any of the sensing electrodes and not only between pairs 2102, 2103 and 2104. As illustrated in the previous embodiment, a patch or urine between any one of the pairs 2102, 2103 and 2104. So, the possible closed circuits that could be detected as per previous embodiment is either closed circuit A, B or C. As per this embodiment of the present invention, since, all the sensing elements are connected to each other, multiple closed circuit could be detected. Thus, the urine patch 2105g as shown in the FIG. 18E forms multiple closed circuit-closed circuit B, closed circuit I, closed circuit D, closed circuit E, closed circuit J and closed circuit K. Similarly, urine patch 2105h would form closed circuit A, closed circuit F, closed circuit J. Thus by electrically coupling each sensing elements, multiple closed circuit could be forced and thus, more accurate information about the spread of the urine patch could be calculated. This helps detect the conductivity of the urine for differing areas across the diaper.

As per yet another embodiment of the present invention, the conductance of the closed circuit formed between the pairs could be tracked to show how the conductance increases or decreases. The change of conductance could be used to calculate increase of urine inside the diaper. The change of conductance could be tracked to know the rate of increase of urine inside the diaper.

Figure 19:
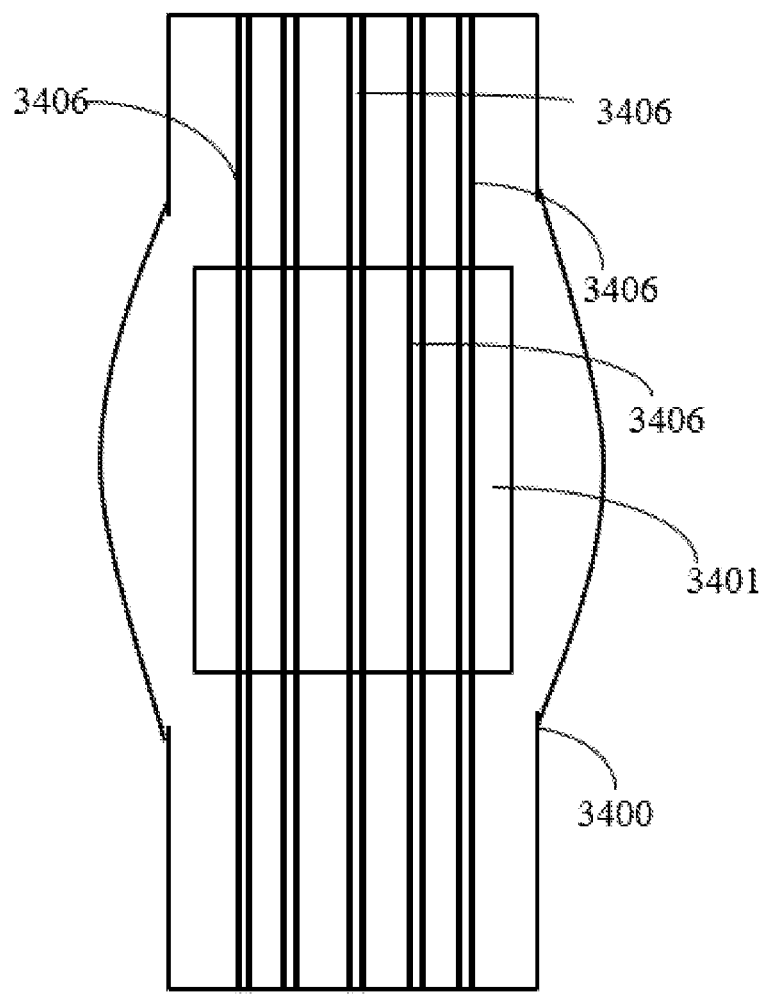
FIG. 19 illustrates a top view of a one of the various different embodiment of the diaper as per the new embodiment.

As per yet another embodiment of the present invention, multiple pairs of electrodes are present on the edges and each pair of electrode could be used to detect the level of urine present at the outer edges of the absorbent pad. FIG. 19 illustrates on such embodiment of the present invention where multiple pairs of sensing electrodes 3406 are present on a bottom layer 3400 of the diaper. The pairs 3406 are spread across the entire width of the central portion 3401 of the bottom layer 3400 where an absorbent pad would be present. Urine presence inside the diaper could be tracked by formation of closed circuit between the pairs of electrodes. The location of the pairs are so chosen that closed circuit will provide the indication of how far the urine has spread inside the absorbent pad. The rate at which new closed circuits are formed could also describe the spreading of the urine inside the diaper.

Figure 20A:
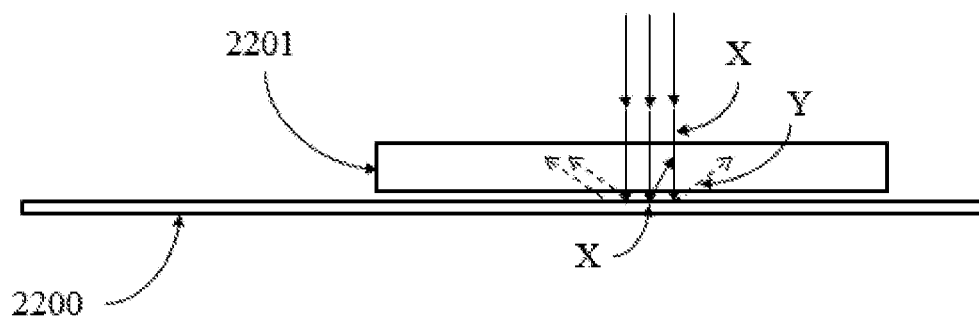
FIGS. 20A-20B illustrate the change of conductance inside a diaper as per the new embodiment of the present invention.
Figure 20B:
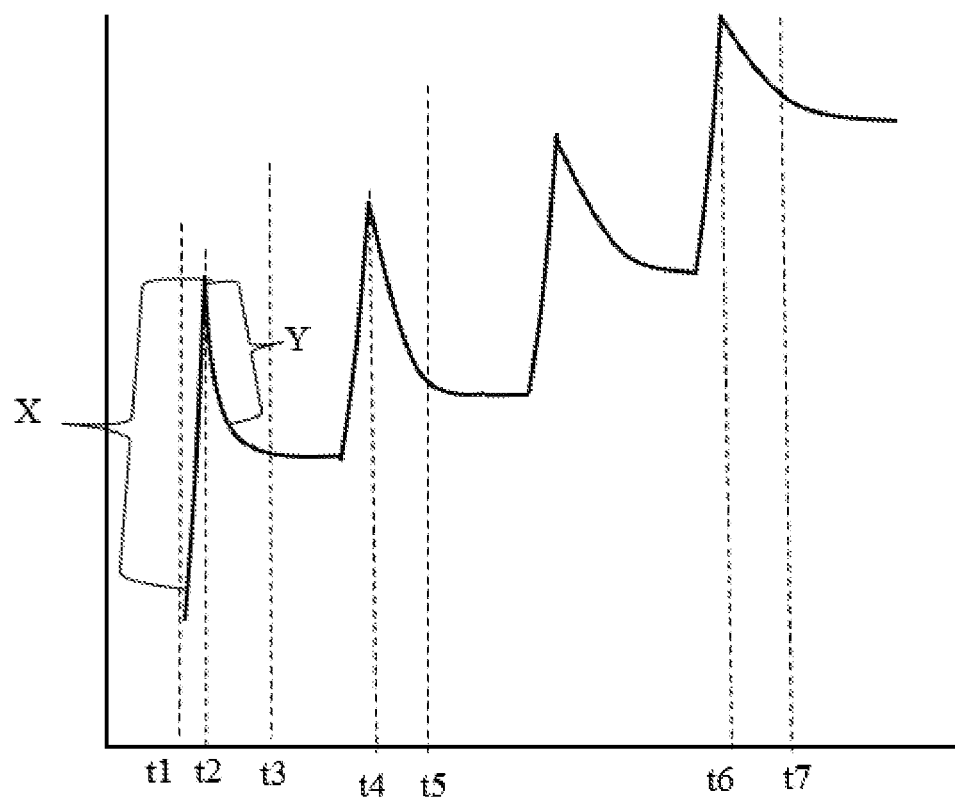

As mentioned in the previous embodiments, the number of closed circuit formed and location of the closed circuits could be used to identify amount of urine present in the diaper. As per this embodiment of the present invention, the detecting device can detect closed circuit formed between any two sensing elements. When urine touches any two sensing elements a closed circuit is formed between them. The conductance of the closed circuit is also tracked by the remote device. This is explained using FIG. 20A and FIG. 20B. FIG. 20A shows the process that follows when a person urinate inside a diaper. Urine flows is shown by arrows in the FIG. 20A. When a person starts to urinate the urine flows through various layers of the diaper. The urine also passes through the absorbent pad 2201 and touches the bottom layer 2100. Thus, closed circuit is formed between sensing elements present on the bottom layer 2100. Till the time a person urinates, more and more urine touches bottom layer 2100 and thus, the conductance between the sensing elements increase. This is shown by the process X. After the person stops urinating, the absorbent pad 2201 starts absorbing the urine up. This is also shown by doted arrows. This is shown by process Y. This causes reduction of conductance of the closed circuit formed by the urine. Thus, increase of conductance of a closed circuit is shown by X and decrease of conductance is shown by Y. FIG. 20B illustrates the conductance of the closed circuit. When a person starts urinating, after time t1 the urine touches the sensing electrodes between any two electrodes and the closed circuit is formed. The conductance of the closed circuit rise steeply with expanding volume of urine, shown by X curve. At time t2, when the person stops urinating, the absorbent pad absorbs the urine, reducing the amount of conductance of the closed circuit between the two sensing electrodes. Thus, the conductance falls steeply at t2 and after some time and is shown by curve Y, the conductance becomes stable or reduces at a very slow rate at time t3. This level at which the conductance becomes stable is the basic amount of urine inside the diaper. The conductance remains at that level as long as the wearer urinates again. When the wearer urinates again, the amount of urine in contact with the two sensing electrodes increase which causes the conductance to rise again. This time the peak point of the conductance will be higher than earlier. After the person stops urinating, the conductance will fall again from the peak position. However, since the diaper is already filled with urine, the absorbent pad will absorb at a slower rate and hence, the rate of decrease in conductance will be less compared to earlier. Further, the level at which the conductance will be stable could be higher than earlier. This level is now the basic amount of urine present inside the diaper. This is shown in the FIG. 20 between time slots t4 and t5. The process gets repeated every time the person urinates as shown in the figure. Every tie, the rate of decrease in conductance will be less compared to earlier and the level at which the conductance becomes stable will increase. After a time, the rate of decrease of conductance is less than a predetermined threshold, it can be ascertained that the diaper is saturated. This is shown between time t6 and t7 in the figure. With increasing amount of urine inside the diaper, the absorbent pad will absorb urine much slower than preceding times and thus, the rate of decrease in conductance will be slower after every time the person urinates. And after a time, when the conductance does not decrease much after a fixed amount of time, it could be ascertained that the diaper is saturated and as a result absorbing at a very low rate. The rate of decrease in conductance indicates the rate of absorption of urine by the absorbent pad. Therefore, there are three more different ways of ascertaining volume and level of saturation inside the diaper—1. When conductance of closed circuit stabilizes, the basic level of urine present inside the diaper compared to other levels over time. 2. The rate of immediate absorption of urine after it reaches a peak conductance or after a person stops urinating. 3. The rate of absorption and degree of absorption over a longer period of time after a conductance becomes more or less stable.

As per yet another embodiment of the invention, the detecting device tracks conductance and rate of change of conductance of all the closed circuits that are formed. All the closed circuits that are formed follows a similar pattern of increase and decrease of conductance as described in the previous embodiments. By tracking increase and decrease of conductance, the amount of urine present at every location of the diaper could be ascertained.

Figure 21A:
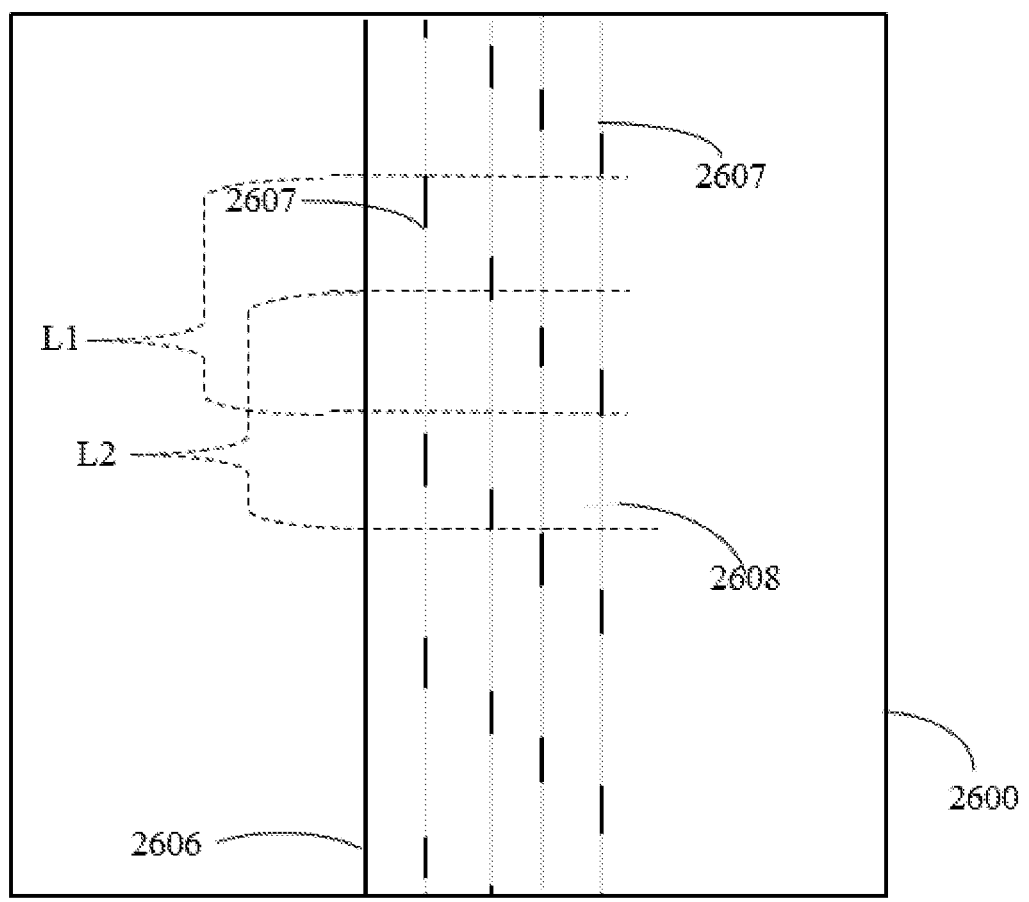
FIGS. 21A-21B illustrate a bottom layer of a diaper as per another embodiment of the present invention.
Figure 21B:
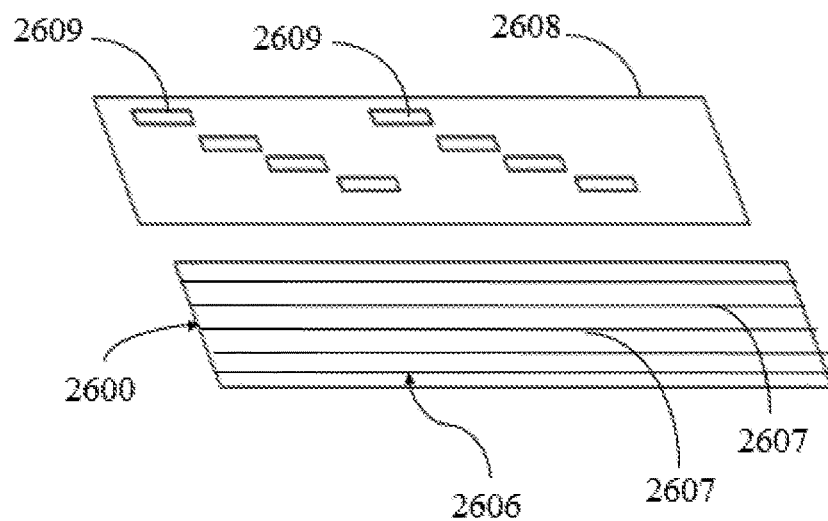

In yet another embodiment of the present invention, an insulation layer is printed on top of the bottom layer. FIG. 21A shows a bottom layer 2600 of a diaper with sensing electrodes. One of the electrodes 2606 is the primary electrode that run across the entire length of the bottom layer 2600. Other electrodes 2607 runs across the entire length of the bottom layer 2600. The number of other electrodes 2607 are four as per this embodiment of the present invention. A insulation layer 2608 is printed on top of the bottom layer 2606 such that it overlaps the other electrodes 2607 and do not overlap the primary electrode 2606. The insulation layer 2608 is printed in such a way that multiple slots 2609 are formed at different places to expose various parts of the other electrodes 2607. The location of the slots 2609 are staggered so that at any location within the layer, not more than two sensing electrodes are exposed, one being 2606 and any one of 2607 electrodes. The purpose of such a structure is that both the insulation layer 2608 and the bottom layer 2600 are generally long rolls of materials that required precise cut at positions. Previously, if the cutting device cut the diaper at different length, a detecting device would not be able to connect all the sensing electrodes. With the insulation layer 2608 having staggered slots 2609 the long rolls could be cut at any location and each piece of the bottom layer 2600 and the insulation layer 2608 would have roughly 4 locations that have electrodes exposed. Further, the cutting device does not have to register the design of the sensing electrode. This is explained in the FIG. 21 A. When a length L1 is cut, the electrodes 2607 are exposed at four different location within the section L1. The length L1 is the length of a diaper. When a same length section L2 is cut at a different location, then it also exposes electrodes at different locations. FIG. 21B illustrates a three dimensional view of the bottom layer 2600 with the electrodes and the insulation lamination layer 2608. The insulation lamination layer 2608 is printed in such a way that multiple slots 2609 are formed throughout the entire length of the layer 2608 in a staggered manner. The slots 2609 expose the electrodes at different places to the moisture present on the absorbent pad. Further, when used with a diaper as per the present invention, the detecting device does not have to know about the design and location of the sensing electrode. In previous designs, the detecting device has to know the design and pattern of the electrodes. With this pattern of slots 2609 exposing sensing electrodes at different non-overlapping positions across the length, the detecting device can connect to all the sensing electrodes and does not have to know the sensing electrodes pattern.

Figure 22A:
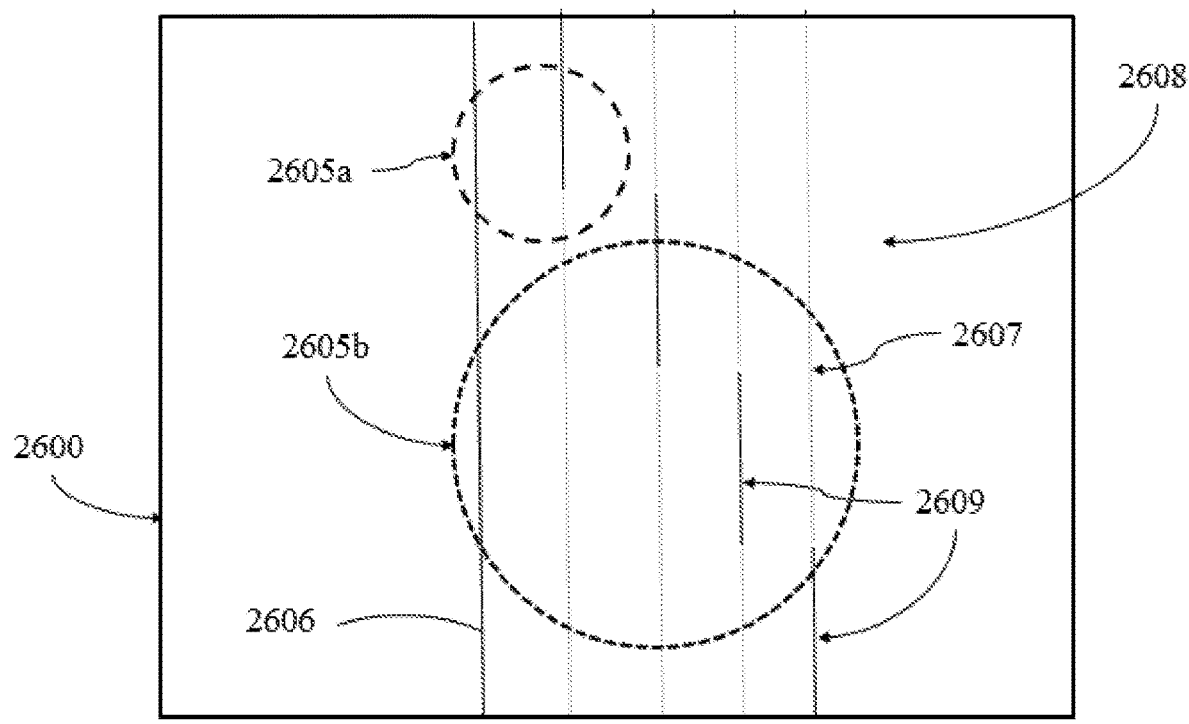

FIG. 22A illustrates the operation of the diaper having the bottom layer 2600 and the insulation lamination layer 2608. When moisture patch 2605a is present, it forms a closed circuit between 2606 and 2607, which is exposed through one of the slots 2609 of the insulation layer 2608. Similarly, when urine patch 2605b is present, it forms closed circuit between different electrodes 2607 at different places exposed by the slots 2609. It must be noted that in one of the embodiments, even the primary electrode 2606 is overlapped by the insulation layer 2608 printed on it and is exposed through different slots. As per one of the embodiments, all the sensing electrode are manufactured by spraying conductive inks on a moving roll of bottom layer as mentioned in the previous embodiments of the present invention. However, as per the primary embodiments of the present invention, the electrodes could be printed using any other method known in the art. Further, the various slots 2609s are manufactured by printing the insulation layer 2608 in specific ways to cover the electrodes 2607 at places and to open them at places in a staggered manner.

Figure 22B:
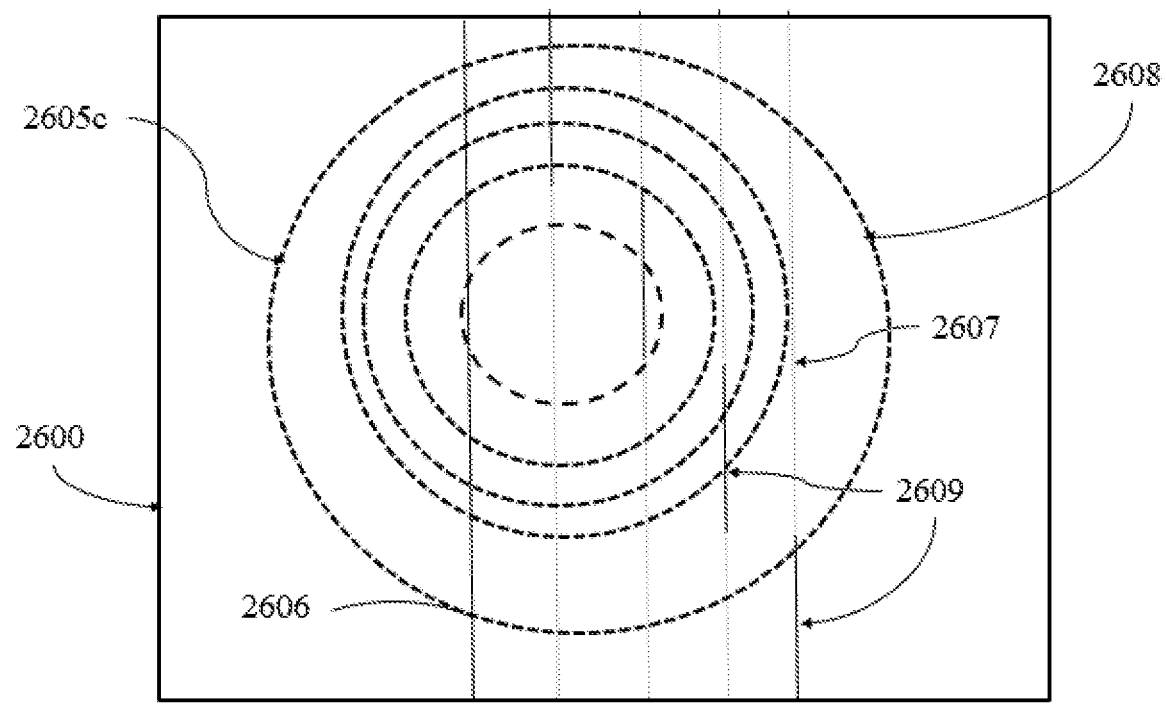

As per yet another embodiment of the present invention, growing amount of urine inside a diaper could be tracked using increasing number of closed circuits that are formed. This is explained using FIG. 22B. When urine patch 2605c was small, it creates a short circuit between one of the electrodes 2607 and 2606. With increasing urine, the size of the patch 2605c also grows as shown by increasing dotted concentric circles. With growing urine patch size, more closed circuits are formed. Thus, the number of closed circuit formed also shows increasing volume of urine inside the diaper. This could be tracked to provide indication of volume of urine present inside the diaper. Thus, with pattern like this, the detecting device just have to see how many closed circuits are formed. This reduces the pre-processing required in existing detecting devices that has to be programmed as per the location and design of the sending electrodes. Thus, presence of urine inside the diaper could be measured using combination of the following information: 1. Absorption rate of the diaper based on decrease of conductance after it reaches its peak. 2. Absolute level of conductance when it stabilizes. 3. The total number and geographic position of the closed circuits that are formed. 4. The absorption rate at after the conductance more or less stabilizes. It must be here noted that decrease in conductance happens in three stages. It is explained using FIG. 22C. Conductance of the closed circuit formed due to urine reaches its peak level till the time user is urinating. After which the absorbent pad soaks in the urine reducing the conductance very quickly over a short span of time. This is shown as phase I in the figure. After that the absorbent pad absorbs the urine in a steady fashion and hence, the conductance decreases slowly over a longer period of time. This is shown as Phase II in the figure. After the absorbent pad absorbs the urine, the conductance level becomes more or less stable. This is shown as phase III in the figure. Measurement of rate of conductance at each of these phases could be utilized to detect absorption rate of the diaper. However, as per one of the primary embodiments of the present invention the rate of absorption is calculated by tracking the rate of change of conductance in phase II.

As per one of the primary embodiments of the present invention, a detecting device is manufactured that is curved. FIG. 23A illustrates a curved detecting device 2300. As mentioned in previous embodiments, the sensing electrodes are present across the entire width of the bottom layer of the diaper and each of the sensing electrodes needs to be connected to a detecting device for detecting closed circuits formed by the urine present inside the diaper. For connecting all the electrodes to the detecting device, the detecting device also should be large enough compared to existing detecting device. In case the detecting device is a flat surface it would be uncomfortable for the user. Hence, the curved detecting device 2300 is manufactured which could be present across a part of the belly of the user in the shape of the belly of the user without causing discomfort. This is shown in FIG. 23B. The diaper spread across most of the frontal width of the wearer. Since, the electrodes are present over a wider area, the detecting device 2300 is made curve so as to get attached to the diaper and also form a curve surface of to cause discomfort to the wearer. Having a flat surfaced detecting device that is big enough to connect to all the electrodes of the diaper, would not be an ergonomic design and would put immense pressure on the belly region of the wearer. Thus, having a curved surface enables the detecting device to be large enough to connect to all the electrodes of the diaper as per the present embodiment and also be ergonomic enough not to cause discomfort to the wearer. The detecting device 2300 has the same set of electronics and have the same functionality as the detecting device mentioned in the previous embodiments of the present invention.

Figure 24:
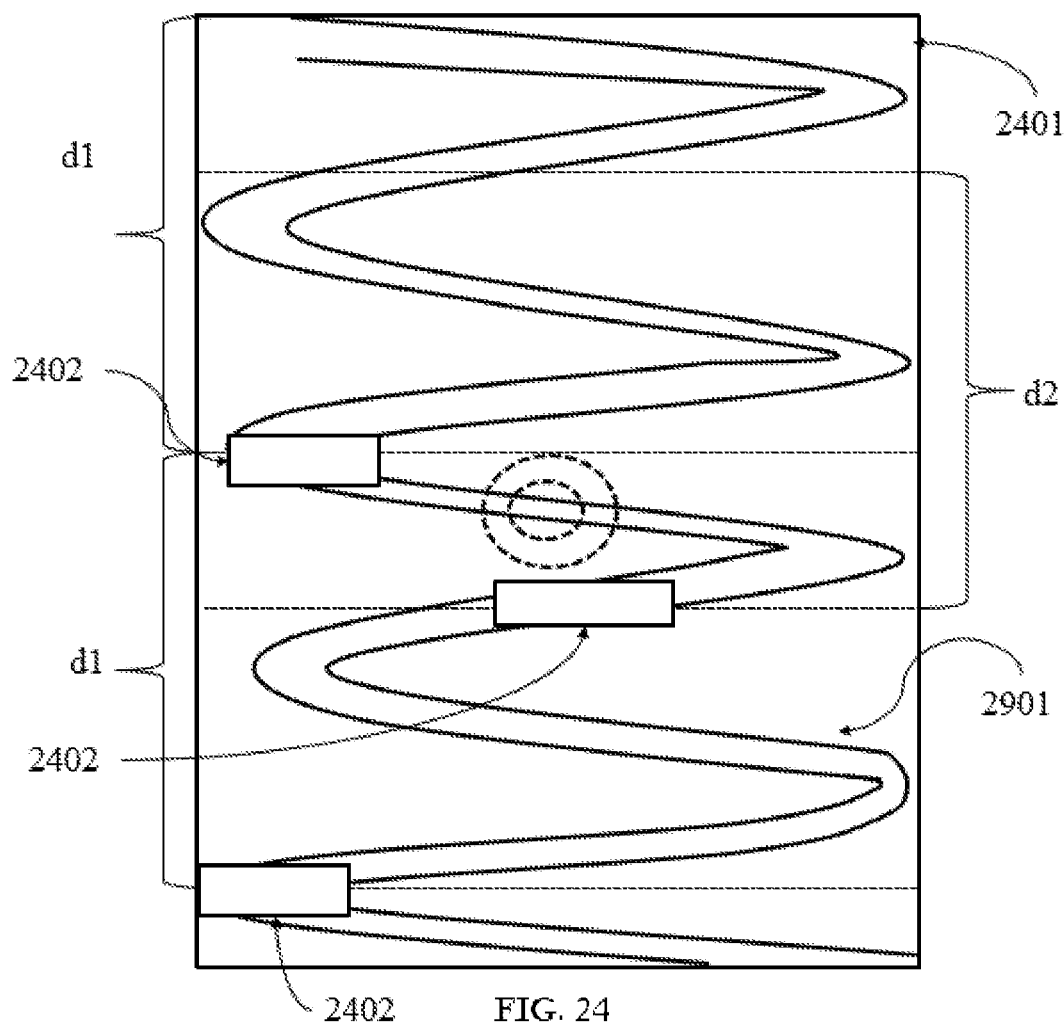
FIG. 24 illustrates a underpad with sensing electrodes as per one of the embodiment of the present invention.

As per yet another embodiment of the present invention, a pair of sensing electrodes is used to detect bodily fluids on a diaper or an underpad. Underpad is a plastic based cloth used over a bed for detecting urine and other bodily fluids discharged by a person sleeping on the bed. It also has an absorbent layer placed on top of the plastic layer. To detect that either electrodes needs to be designed in a specific pattern or the detecting device have to be large enough to connect to all the electrodes spread across the entire width of the underpad. With specifically designed sensing electrodes, the underpad that is made from one or multiple sheets, the electrodes need to be patterned and the sheet of underpad needs to be cut at precise locations. As per this embodiment of the present invention, the underpad can be cut at any location on the sheet from which underpad is made and have a small detecting device which can be clipped. The cutting device does not have to pre-register the pattern of the sensing electrode which is the primary utility of this embodiment of the present invention. The sensing electrode is patterned in such a way that the roll of the sheet can be cut at any location and every piece will have the same pattern of sensing electrode. FIG. 24 shows an underpad sheet 2401 with a pair of sensing electrodes 2901 that is preprinted on the entire sheet. The sensing electrodes 2901 are designed to cover the entire width of the underpad sheet 2401 by traversing a serpentine like design without touching each other. As per yet another embodiment of the present invention, the design can be sinusoidal type design or a triangular waveform design. It must here be noted that the gap between the two electrodes of the pair 2901 should be uniform. Having such a design helps in locating moisture that is present at any location on the underpad. Now, when a length d1 of the sheet 2401 is cut for an underpad, a detecting device 2402 could be clipped on to only the portion where the pair 2901 is terminating for that underpad. Similarly, when the underpad sheet 201 is cut at position d2 for a same length of underpad, the same detecting device could be clipped to at the terminating end of the pair 2901 for that underpad. As shown in the figure, d1 and d2 can be cut at any different position. Thus, using this design, the single sheet of underpad 2401 can be cut at any location to make an underpad and the detecting device has to be clipped on to it without requiring any registration. Further, the detecting device just have to locate a closed circuit and does not need to be preprogrammed as per specific designs of the underpad. The closed circuit is formed when urine or similar body-fluid is present between the electrode pair 2901. This is represented by the patch 2902. With increase in volume of urine, the patch increases and similarly the conductance increases. The detecting device clipped to underpad is electrically coupled to the pair 2901 and can detect formation of the closed circuit and change in conductance with growing volume of urine. Thus, the detecting device can detect present of moisture and amount of moisture without requiring any registration. Further, the detecting device 2402 could be used to track change of conductance or resistance caused due to increasing amount of urine present on the underpad, using any one of the method explained in previous embodiments of the present invention.

It will now be readily appreciated that the present invention may be used to advantageously sense wet conditions on items other than diapers, including, without limitation, surgical dressings, bed coverings, clothing, skin, etc. Also, it should now be understood that body fluids of all types can be sensed, initiating the signal produced by the invention, including, without limitation, urine, blood, saliva, sweat, vomits, mucus, semen, tears, milk and feces, and water, all of which are electrolytic in varying degrees.

The invention may be used for a variety of applications. In addition to quickly alerting a caretaker that a user of a diaper within their care has excreted a body fluid, the device may be used in conjunction with urine receptacles positioned within the diapers for catching urine for analysis. It is frequently desirable to perform bacterial analysis, such as a bacteria count, on such collected samples, and the results may be skewed if the urine sits for long periods and the bacteria multiply. It can also be used to identify the number of times a user is excreting urine that could help identify other health conditions like diabetes.

The invention claimed is:

1. A method of manufacturing a diaper, the method comprising:
   providing three pairs of electrodes on a bottom layer of a diaper;
      wherein the placement of the three pairs of electrodes is chosen selectively;
   cutting the bottom layer at any location,
   wherein the three pairs of electrodes runs the entire length of the diaper, wherein the placement is that a pair of electrodes is present at or near the center of the bottom layer and two pairs of electrodes are placed at or near two lateral edges of a central portion of the bottom layer, wherein the central portion is a region over which an absorbent pad is placed.

2. The method as in claim 1, wherein the three pairs of electrodes are manufactured by spraying conductive inks on a moving roll of layer of the diaper.

3. The method as in claim 1, wherein the placement is near at least one of the edges of a central portion of the bottom layer, wherein the central portion is a region over which an absorbent pad is placed.

4. The method as in claim 1, wherein a detecting device can detect a closed circuit formed by a body fluid present between the three pairs of electrodes.

5. The method as in claim 4, wherein the detecting device can detect saturation level of the diaper.

6. The method as in claim 4, wherein the detecting device can detect absorption rate of the diaper.

7. The method as in claim 1, wherein the manufacturing is done by a machine, wherein the machine can cut the bottom layer at any location.

* * * * *